(12) United States Patent
Su et al.

(10) Patent No.: US 8,623,839 B2
(45) Date of Patent: *Jan. 7, 2014

(54) COMPOSITIONS AND METHODS FOR STABILIZED POLYSACCHARIDE FORMULATIONS

(75) Inventors: Dongling Su, Franklin, MA (US); Julia Hwang, Wayland, MA (US); Brooks J. Story, Franklin, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/173,658

(22) Filed: Jun. 30, 2011

(65) Prior Publication Data

US 2013/0005681 A1    Jan. 3, 2013

(51) Int. Cl.
*A61K 31/728* (2006.01)
*A61K 31/7004* (2006.01)
*A61K 47/26* (2006.01)
*A61K 9/19* (2006.01)
*A61P 29/00* (2006.01)

(52) U.S. Cl.
USPC .......................................................... 514/54

(58) Field of Classification Search
USPC .......................................................... 514/54
See application file for complete search history.

(56) References Cited

U.S. PATENT DOCUMENTS

| | | | |
|---|---|---|---|
| 3,697,652 A | 10/1972 | Rovati et al. | |
| 4,141,973 A | 2/1979 | Balazs | |
| 4,666,897 A | 5/1987 | Golub et al. | |
| 5,011,691 A | 4/1991 | Oppermann et al. | |
| 5,143,724 A | 9/1992 | Leshchiner et al. | |
| 5,258,371 A | 11/1993 | Golub et al. | |
| 5,266,683 A | 11/1993 | Oppermann et al. | |
| 5,273,056 A | 12/1993 | McLaughlin et al. | |
| 5,364,845 A | 11/1994 | Henderson | |
| 5,366,964 A | 11/1994 | Lindstrom et al. | |
| 5,399,351 A | 3/1995 | Leshchiner et al. | |
| 5,409,904 A | 4/1995 | Hecht et al. | |
| 5,498,606 A | 3/1996 | Soll et al. | |
| 5,510,121 A | 4/1996 | Rhee et al. | |
| 5,789,395 A | 8/1998 | Amin et al. | |
| 5,792,103 A * | 8/1998 | Schwartz et al. ............... 604/82 |
| 5,814,621 A | 9/1998 | Kanaya et al. | |
| 6,030,635 A | 2/2000 | Gertzman et al. | |
| 6,051,560 A | 4/2000 | Chang et al. | |
| 6,069,135 A | 5/2000 | Falk et al. | |
| 6,197,326 B1 | 3/2001 | Suzuki et al. | |
| 6,238,372 B1 | 5/2001 | Zinger et al. | |
| 6,281,195 B1 | 8/2001 | Rueger et al. | |
| 6,288,043 B1 | 9/2001 | Spiro et al. | |
| 6,346,519 B1 | 2/2002 | Petrus | |
| 6,410,044 B1 | 6/2002 | Chudzik et al. | |
| 6,428,804 B1 | 8/2002 | Suzuki et al. | |
| 6,437,018 B1 | 8/2002 | Gertzman et al. | |
| 6,458,375 B1 | 10/2002 | Gertzman et al. | |
| 6,551,801 B1 | 4/2003 | Andou et al. | |
| 6,586,406 B2 | 7/2003 | Heidaran et al. | |
| 6,608,043 B1 | 8/2003 | Serizawa et al. | |
| 6,656,925 B2 | 12/2003 | Petrus | |
| 6,677,321 B1 | 1/2004 | Levin | |
| 6,699,471 B2 | 3/2004 | Radice et al. | |
| RE38,522 E | 5/2004 | Gertzman et al. | |
| 6,756,358 B2 | 6/2004 | Iwamoto et al. | |
| 6,818,629 B2 | 11/2004 | Peterson et al. | |
| 6,835,377 B2 | 12/2004 | Goldberg et al. | |
| 6,906,044 B2 | 6/2005 | Hermida Ochoa | |
| 6,911,212 B2 | 6/2005 | Gertzman et al. | |
| 6,924,273 B2 * | 8/2005 | Pierce ............................ 514/54 |
| 6,924,370 B2 | 8/2005 | Chudzik et al. | |
| 6,949,525 B2 | 9/2005 | Hermida | |
| 6,972,321 B1 | 12/2005 | Hotten et al. | |
| 6,979,679 B2 | 12/2005 | Marcum | |
| 7,019,192 B2 | 3/2006 | Gertzman et al. | |
| 7,025,959 B1 | 4/2006 | Hotten et al. | |
| 7,026,292 B1 | 4/2006 | Lee et al. | |
| 7,045,141 B2 | 5/2006 | Merboth et al. | |
| 7,067,144 B2 | 6/2006 | Demopulos et al. | |
| 7,070,942 B2 | 7/2006 | Heidaran et al. | |
| 7,112,578 B2 | 9/2006 | Levin | |
| 7,141,545 B2 | 11/2006 | Pike et al. | |
| 7,189,392 B1 | 3/2007 | Kim et al. | |
| RE39,587 E | 4/2007 | Gertzman et al. | |
| 7,214,667 B2 | 5/2007 | Fukuda et al. | |
| 7,223,744 B2 | 5/2007 | Yerxa et al. | |
| 7,239,908 B1 | 7/2007 | Alexander et al. | |
| 7,268,114 B2 | 9/2007 | Makishima et al. | |
| 7,314,636 B2 | 1/2008 | Caseres et al. | |
| 7,323,445 B2 | 1/2008 | Zhang et al. | |
| 7,351,798 B2 | 4/2008 | Margolin et al. | |
| 7,425,573 B2 | 9/2008 | Pelletier et al. | |
| 7,485,629 B2 * | 2/2009 | Marcum ........................ 514/52 |
| 7,582,311 B1 | 9/2009 | Cleland et al. | |
| 7,592,009 B2 | 9/2009 | Hubbell et al. | |

(Continued)

FOREIGN PATENT DOCUMENTS

DE    20 2007 011252 U1    12/2007
EP       0 517 970 A1    12/1992

(Continued)

OTHER PUBLICATIONS

United Sugars Corporation, 2010, p. 1.*

(Continued)

*Primary Examiner* — Shaojia Anna Jiang
*Assistant Examiner* — Ganapathy Krishnan

(57) ABSTRACT

Compositions and methods are provided for treating joint conditions, such as osteoarthritis and/or the pain associated therewith. The compositions and methods utilize a first component, namely hyaluronic acid ("HA"), in combination with at least one stabilizer. The composition can include a stabilizer that increases the stability and shelf-life of the HA. In another embodiment, the compositions and methods can also include an additional component, such as one or more glycosaminoglycans ("GAG") or GAG precursors. Examples of GAGs or GAG precursors can include chondroitin sulfate ("CS"), dermatan sulfate, heparin, heparan sulfate, keratan sulfate, and glucosamine ("GlcN").

19 Claims, 9 Drawing Sheets

(56) References Cited

U.S. PATENT DOCUMENTS

| | | | |
|---|---|---|---|
| 7,608,580 B2 | 10/2009 | Kim et al. | |
| 7,651,682 B2 | 1/2010 | Devore et al. | |
| 7,651,703 B2 | 1/2010 | Cleland et al. | |
| 7,763,116 B2 * | 7/2010 | Carter et al. | 127/46.1 |
| 7,931,030 B2 | 4/2011 | Bailleul | |
| 8,398,611 B2 | 3/2013 | Hwang et al. | |
| 2003/0031697 A1 | 2/2003 | Chudzik et al. | |
| 2003/0086899 A1 | 5/2003 | Jafari | |
| 2003/0181371 A1 | 9/2003 | Hunter et al. | |
| 2003/0223983 A1 | 12/2003 | Sofia et al. | |
| 2004/0038929 A1 | 2/2004 | Fukuda et al. | |
| 2004/0082540 A1 | 4/2004 | Hermida Ochoa | |
| 2004/0147466 A1 | 7/2004 | Barman et al. | |
| 2004/0214793 A1 | 10/2004 | Hermida Ochoa | |
| 2004/0241248 A1 | 12/2004 | Margalit et al. | |
| 2005/0025765 A1 | 2/2005 | DiMauro et al. | |
| 2005/0100538 A1 | 5/2005 | Mohamed et al. | |
| 2005/0112186 A1 | 5/2005 | Devore et al. | |
| 2005/0232981 A1 | 10/2005 | Ben-Sasson | |
| 2005/0250737 A1 | 11/2005 | Hughes et al. | |
| 2006/0040894 A1 | 2/2006 | Hunter et al. | |
| 2006/0073207 A1 | 4/2006 | Masters et al. | |
| 2006/0122147 A1 * | 6/2006 | Wohlrab | 514/54 |
| 2006/0122150 A1 | 6/2006 | Argentieri et al. | |
| 2006/0210552 A1 | 9/2006 | Demopulos et al. | |
| 2007/0053987 A1 | 3/2007 | Bayer et al. | |
| 2007/0149441 A1 | 6/2007 | Aeschlimann et al. | |
| 2007/0172517 A1 | 7/2007 | Ben-Sasson et al. | |
| 2007/0190149 A1 | 8/2007 | Zahos | |
| 2007/0203095 A1 | 8/2007 | Sadozai et al. | |
| 2007/0275055 A1 | 11/2007 | Ben-Sasson et al. | |
| 2007/0286881 A1 | 12/2007 | Burkinshsw | |
| 2008/0118523 A1 | 5/2008 | Hubbell et al. | |
| 2008/0145404 A1 | 6/2008 | Hill et al. | |
| 2008/0147065 A1 | 6/2008 | McKay et al. | |
| 2008/0147077 A1 | 6/2008 | Garigapati et al. | |
| 2008/0167235 A1 | 7/2008 | Zhang et al. | |
| 2009/0017091 A1 | 1/2009 | Daniloff et al. | |
| 2009/0017093 A1 | 1/2009 | Springer et al. | |
| 2009/0035315 A1 | 2/2009 | Christgau et al. | |
| 2009/0087503 A1 | 4/2009 | Henderson et al. | |
| 2009/0099089 A1 | 4/2009 | Zhang et al. | |
| 2009/0104148 A1 | 4/2009 | Jay et al. | |
| 2009/0118348 A1 | 5/2009 | Miyamoto et al. | |
| 2009/0123547 A1 | 5/2009 | Hill et al. | |
| 2009/0124552 A1 | 5/2009 | Hill et al. | |
| 2009/0136576 A1 | 5/2009 | Calvosa et al. | |
| 2009/0162351 A1 | 6/2009 | Brown et al. | |
| 2009/0162376 A1 | 6/2009 | Brown et al. | |
| 2009/0181007 A1 | 7/2009 | Gennero et al. | |
| 2009/0181058 A1 | 7/2009 | Li et al. | |
| 2009/0202430 A1 | 8/2009 | Hoemann et al. | |
| 2009/0202642 A1 | 8/2009 | Huang et al. | |
| 2009/0291112 A1 | 11/2009 | Truncale et al. | |
| 2010/0217231 A1 | 8/2010 | Ilan et al. | |
| 2012/0165257 A1 | 6/2012 | Byers et al. | |
| 2012/0165731 A1 | 6/2012 | Byers et al. | |
| 2012/0165787 A1 | 6/2012 | Hwang et al. | |

FOREIGN PATENT DOCUMENTS

| | | |
|---|---|---|
| EP | 2 033 689 A1 | 3/2009 |
| EP | 2251359 A1 | 11/2010 |
| FR | 2866571 A1 | 8/2005 |
| JP | 11-302197 A | 11/1999 |
| JP | 2003-160464 A | 6/2003 |
| JP | 2004-359629 A | 12/2004 |
| JP | 3-748970 B2 | 2/2006 |
| KR | 2008-0024426 A | 3/2008 |
| WO | 94/28889 A1 | 12/1994 |
| WO | 97/24374 A1 | 7/1997 |
| WO | 97/28788 A1 | 8/1997 |
| WO | 98/22114 A1 | 5/1998 |
| WO | 99/40926 A1 | 8/1999 |
| WO | 03/034993 A2 | 5/2003 |
| WO | 03/043660 A2 | 5/2003 |
| WO | 2004/032943 A1 | 4/2004 |
| WO | 2005/110439 A2 | 11/2005 |
| WO | 2008/098019 A2 | 8/2008 |
| WO | 2009/005790 A2 | 1/2009 |
| WO | WO 2009/00570 A2 * | 1/2009 |
| WO | WO 2009024670 A2 * | 2/2009 |
| WO | 2009132228 | 10/2009 |
| WO | 2011/086458 A1 | 7/2011 |

OTHER PUBLICATIONS

Benaroudj et al, The J. Biol. Chem. 2001, 276(26), 24261-67.*
Mankin, H.J et al, The Journal of Clinical Investigation, 1971, 50, 1712-1719.*
Greenfield Pharmacy, 1999, paes 1-2.*
Extended European Search Report issued Mar. 20, 2012 for Application No. 11195499.6 (5 Pages), pp. 1-5.
Minutoli, SHOCK, vol. 27(1), 91-96 (2007).
Chen, J Exp Biol, 207, 3125-3129 (2004).
Birch, Advances in Carbohydrate Chem, vol. 18, 201-225 (1963).
Hoelzle, Applied Env Microbiol, vol. 56, 3,213-3,215 (1990).
Benaroudj et al., Biol Chem. 2001;276:24261-7.
Yoshizane et al., Nutrition Res. 2000;20:1485-91.
Celeste et al. PNAS 87:9843-47 (1990).
Cheng et al. "Osteogenic activity of the fourteen types of human bone morphogenetic proteins" J. Bone Joint Surg. Am. 85A: 1544-52 (2003).
Honda, et al, Journal of Bioscience and Bioengineering 89(6), 582-589 (2000).
Lyons et al. PNAS 86:4554-58 (1989).
Massague Annu. Rev. Cell Biol. 6:957 (1990).
Orthovisc® manufactured by Anika Therapeutics, Inc. of Bedford, MA product, 2 pages, 2011.
Ozkaynak et al. EMBO J. 9:2085-93 (1990).
Ruppert, et al Eur J Biochem 237, 295-302 (1996).
Sampath, et al. J. Biol. Chem. 265:13198 (1990).
Wharton, et al. PNAS 88:9214-18 (1991).
Remington's Pharmaceutical Sciences, 15th ed. Easton: Mack Publishing Co.: 1405-1412, 1461-1487, 1975.
The National Formulary XIV., 14th ed. Washington: American Pharmaceutical Association, 1975 Table of Contents only, pp. 1-7.
Goodman and Gilman's The Pharmacological Basis for Therapeutics (7th ed.) Table of Contents only, pp. 1-5.
[no. Author Listed] Euflexxa® Product information sheet. May, 2011, 2 pages.
[no. Author Listed] Orthovisc® detailed product information. Jun. 2005, 2 pages. Retrieved Apr. 25, 2012 from <http://www.depuy.com/sites/default/files/products/files/OrthoviscNonAvianPIFinal2010.pdf>.
[no. Author Listed] Shiseido. Sodium Hyaluronate. Medical Grade. 1993, 4 pages.
European Partial Search Report for Application No. 12174614.3, issued Aug. 14, 2012. (9 pages).
Rohanizadeh et al., Hydroxyapatite as a carrier for bone morphogenetic protein. J Oral Implantol. Dec. 2011;37 (6):659-72. doi: 10.15631AAID-JOI-D-10-00005. Epub Jul. 21, 2010.

* cited by examiner

COMPOSITIONS AND METHODS FOR STABILIZED POLYSACCHARIDE FORMULATIONS

FIELD OF THE INVENTION

The present invention relates generally to compositions and methods for treating joints.

BACKGROUND OF THE INVENTION

Osteoarthritis ("OA"), the most common form of arthritis, is a type of arthritis that is characterized by degenerative (gradual deterioration of joint) or abnormal changes in bone, cartilage, and synovium of the joints. OA is often characterized by a progressive wearing down of opposing joint surfaces accompanied at times by inflammation resulting in pain, swelling, and stiffness for the patient. OA can occur in one or more joints following trauma to the joint, following an infection of the joint, or simply as a result of aging. Furthermore, there is emerging evidence that abnormal anatomy, genetics, and obesity may contribute to early development of OA.

Treatment of OA generally involves a combination of exercise, physical therapy, lifestyle modification, and analgesics. Acetaminophen is typically the first line treatment for OA. For mild to moderate symptoms, effectiveness is similar to non-steroidal anti-inflammatory drugs ("NSAIDs"), such as ibuprofen. For more severe symptoms NSAIDs may be more effective. However, while more effective, NSAIDs in severe cases are associated with greater side effects such as gastrointestinal bleeding and renal complications. Another class of NSAIDs, COX-2 selective inhibitors (such as Celecoxib), are equally effective to NSAIDs but no safer in terms of side effects. There are several NSAIDs available for topical use, including diclofenac. Typically, they have less systemic side-effects than oral administration and at least some therapeutic effect. While opioid analgesics, such as morphine and fentanyl, improve pain this benefit is outweighed by frequent adverse events and thus they are not routinely used. Intra-articular steroid injections are also used in the treatment of OA, and they are very effective at providing pain relief, especially in patients exhibiting inflammatory elements of OA. However, the duration of the pain relief is limited to 4-6 weeks and there are adverse effects that may include collateral cartilage damage. If pain becomes debilitating, joint replacement surgery may be used to improve mobility and quality of life. There is no proven treatment to slow or reverse the disease.

For patients who do not get adequate pain relief from simple pain relievers, like acetaminophen or from exercise and physical therapy, intra-articular injections of hyaluronic acid (HA) provide another treatment option to address symptomatic pain and may delay the need for a total joint replacement surgery. It is known that the concentration and molecular weight of native HA is deficient in individuals suffering from OA and therefore joint injections of exogenous HA is believed to replenish these molecules and restore the viscoelastic properties of synovial fluid. It is this property that is responsible for lubricating and cushioning the joints. There is also evidence that HA has biological activity through binding to cell surface receptors and may have a role in mitigating inflammation and cartilage degradation. Regardless of the mechanism of action, pain relief is observed for about six months following a treatment course. A treatment course for HA products on the US market can range from a single injection to others that require 3 to 5 weekly injections to attain this durability of pain relief.

Currently, hyaluronic acid ("HA") formulations on the market in the United States are commercialized as ready-to-use liquid HA solutions in prefilled syringes. They can be stored at room temperature, and typically have a two year shelf life. While HA of low to moderate molecular weight can be effective, high molecular weight HA formulas can provide additional benefits, especially at higher HA concentrations. However, the HA in solution is known to degrade over time at room temperature, as measured by reduction in HA molecular weight which could impact its efficacy as an OA therapy.

There remains a need for improved methods and compositions for treating joints, and in particular to improved methods and compositions for treating joints using high molecular weight HA, alone or combined with additional components, to address stability and shelf-life problems associated with current treatments.

SUMMARY OF THE INVENTION

Compositions and methods are provided for treating joint conditions, such as osteoarthritis and/or the pain associated therewith. The methods and compositions disclosed herein are generally directed to treatments of joints utilizing a first component, namely hyaluraonic acid ("HA"), in combination with at least one stabilizer.

In one aspect, formulations or compositions are disclosed for treating a joint condition comprising a formulation. The formulation or composition can be in liquid form. The formulation can also be stable at room temperature. Moreover, the formulation can include a solution of hyaluronic acid (HA). The HA formulation can be a high molecular weight HA. The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000 kDa or more, or any range derivable therein. In exemplary embodiments, the HA has a molecular weight in the range of about 1 MDa to 6 MDa. In another exemplary embodiment, the HA has a molecular weight greater than 1 MDa.

Moreover, the HA formulation can be present at particular concentrations either in liquid, solid or lyophilized form. In one embodiment, the HA is present at a liquid concentration of at least about 1 mg/ml. In another exemplary embodiment, the HA has a liquid concentration of at least about 5 mg/ml, and more preferably at least about 7 mg/ml, and more preferably at least about 10 mg/ml, and more preferably at least about 15 mg/ml, and in some embodiments the concentration can be at least about 25 mg/ml. In another embodiment, the HA can have a concentration in the range of about 15 mg/ml to about 25 mg/ml.

In another aspect, the formulation or composition includes at least one additional component. The additional component added to the formulation or composition can be, for example, amino acids, amino sugars, sugar alcohols, proteins, saccharides, di-saccharides, oligo-saccharides, poly-saccharides, nucleic acids, buffers, surfactants, lipids, liposomes, other excipients, and mixtures thereof. Other useful components can include steroids, anti-inflammatory agents, non-steroidal anti-inflammatory agents, analgesics, cells, antibiotics, antimicrobial agents, anti-inflammatory agents, growth factors, growth factor fragments, small-molecule wound healing stimulants, hormones, cytokines, peptides, antibodies, enzymes, isolated cells, platelets, immunosuppressants, nucleic acids, cell types, viruses, virus particles, essential nutrients, minerals, metals, or vitamins, and combinations thereof. Additionally, the formulation or composition can include a diluent, such as water, saline, or a buffer.

In an exemplary embodiment, the formulation or composition includes at least one stabilizer or stabilizing excipient, such as tocopherol, tocopherol derivatives, mannitol, glucose, sucrose and trehalose. The stabilizers can be present in a range of about 0.1-70% by weight; about 0.1-50% by weight, about 0.1-20% by weight; or about 0.5-20% by weight. Alternatively, the excipient can be present at a concentration in a range of about 1 mg/ml to about 700 mg/ml, and more preferably in a range of about 1 mg/ml to about 500 mg/ml, and more preferably in a range of about 1 mg/ml to about 200 mg/ml, and more preferably in a range of about 5 mg/ml to about 200 mg/ml.

In another aspect, the formulation or composition includes at least one additional component, such as a glycosaminoglycan (GAG), including GAGs like chondroitin sulfate ("CS"), dermatan sulfate, heparin, heparan sulfate, and keratan sulfate, or a GAG precursor such as glucosamine ("GlcN"). In one embodiment, a GAG or GAG precursor can be present in the composition at a concentration of at least about 0.1 mg/ml, and more preferably at least about 2 mg/ml, and more preferably at least about 5 mg/ml, and more preferably at least about 7 mg/ml, and more preferably at least about 20 mg/ml. In another embodiment, the GAGs can have various molecular weights, but in certain exemplary embodiments the molecular weight is in the range about 5 to 1,000 kDa, more preferably in the range of about 6 to 500 kDa, more preferably in the range of about 7 to 300 kDa, more preferably in the range of about 8 to 200 kDa, more preferably in the range of about 9 to 100 kDa, and most preferably in the range of about 10 to 80 kDa. In other embodiments, the molecular weight of a GAG fragment can be below about 5 kDa and even more preferably below about 3 kDa. In another embodiment, the GAG precursor can have a molecular weight of about 180 Da. In other embodiments, the GAG precursor can have a molecular weight of at least about 100 Da. In an exemplary embodiment, the GAG precursor can have a molecular weight in the range of about 100 Da to about 250 Da.

Moreover, the formulation or composition can have a weight ratio of HA to stabilizer in the range of about 1:0.001 to about 1:100, and more preferably at a ratio in the range of about 1:0.0125 to about 1:10 about 1:0.00125 to about 1:100, and more preferably at a ratio in the range of about 1:0.01 to about 1:10. Alternatively, the formulation or composition can include about 1% to about 75% or more by weight of each of the individual components, e.g. HA and stabilizer.

One more aspect can include a kit and methods of using the kit. The kit can include a solution of high molecular weight hyaluronic acid (HA) and at least one stabilizer. The kit can be stored at room temperature. Additionally, the kit can include a syringe containing the HA solution and the stabilizer in a single chamber. Another embodiment can include a single chamber with the HA solution and stabilizer and a separate chamber with an additional component, such as a GAG or GAG precursor. For example, a glycosaminoglycan (GAG) can be present in the kit in a separate chamber from the HA/stabilizer solution. The additional component can be present in liquid, solid or lyophilized form. The kit can further include a diluent, such as water, saline, and a buffer, to solubilize one of the components, the additional component.

In an additional aspect, a method for treating joints is disclosed that includes administering a liquid formulation comprising high molecular weight hyaluronic acid to a subject in need. The method can include the high molecular weight hyaluronic acid in the presence of a stabilizer. In addition, the high molecular weight hyaluronic acid can be stored in a liquid formulation at room temperature prior to administration. The method can also include administering the solution of HA present in the kit or present in the formulation or composition of high molecular weight HA.

BRIEF DESCRIPTION OF THE DRAWINGS

The appended drawings have been included herein so that the above-recited features, advantages and objects will become clear and can be understood in detail. These drawings form a part of the specification. It is to be noted, however, that the appended drawings illustrate exemplary embodiments and should not be considered to limit the scope.

DETAILED DESCRIPTION OF THE INVENTION

Figure 1:
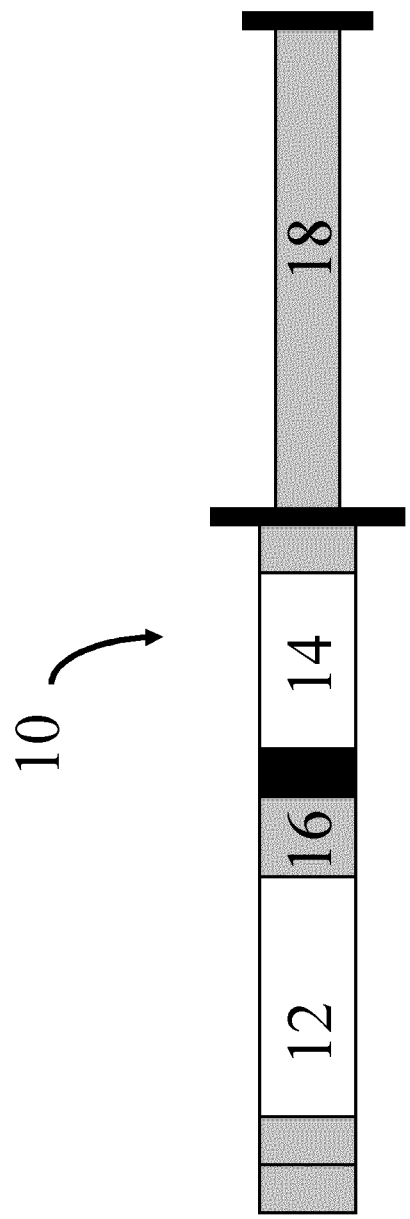
FIG. 1 is a schematic view of one embodiment of a mixing and delivery system for use with the compositions and methods of the present invention.

In general, the present invention provides compositions and methods for treating joint conditions, such as osteoarthritis and/or the pain associated therewith. The compositions and methods utilize a first component, namely high molecular weight hyaluronic acid ("HA"), alone or in combination with an additional component, combined with a stabilizer to prolong shelf-life. In an exemplary embodiment, the composition includes a stabilizer or stabilizing excipient to stabilize HA and, if present, a GAG or GAG precursor.

Hyaluronic Acid

Hyaluronic acid (HA) can have various formulations and can be provided at various concentrations and molecular weights. The terms "hyaluronic acid," "hyaluronan," "hyaluronate," and "HA" are used interchangeably herein to refer to hyaluronic acids or salts of hyaluronic acid, such as the sodium, potassium, magnesium, and calcium salts, among others. These terms are also intended to include not only pure hyaluronic acid solutions, but hyaluronic acid with other trace elements or in various compositions with other elements. The terms "hyaluronic acid," "hyaluronan," and "HA" encompass chemical or polymeric or cross-linked derivatives of HA. Examples of chemical modifications which may be made to HA include any reaction of an agent with the four reactive groups of HA, namely the acetamido, carboxyl, hydroxyl, and the reducing end. The HA used in the present application is intended to include natural formulations (isolated from animal tissue) or synthetic formulations (derived from bacterial fermentation) or combinations thereof. The HA can be provided in liquid form or solid formulations that is reconstituted with a diluents to achieve an appropriate concentration HA is a glycosaminoglycan (GAG), and in particular HA is an unbranched polysaccharide made up of alternating glucuronic acid and N-acetyl glucosamine units. In liquid form, the HA has viscoelastic properties. HA is also found in the extracellular matrix of cartilage as an important structural component of aggrecan, which make up the proteoglycan complex. The major function of the proteoglycan complex is to retain water in the cartilage matrix, imparting its characteristic turgidity and mechanical resiliency.

HA not only helps to maintain healthy mechanical properties of cartilage that cushions joints, but it is also a major component of synovial fluid.

HA abnormalities are a common thread in connective tissue disorders. HA can thus be used to prevent, treat, or aid in the surgical repair of connective tissue disorders.

HA can be used in the compositions and methods of the present invention at various molecular weights. Since HA is a polymeric molecule, the HA component can exhibit a range of molecular weights, and almost any average of modal molecular weight formulation of HA can be used in the compositions and methods of the present invention, including Low Molecular Weight ("LWM") Hyaluronan (about 500 to 700 kilodaltons (kDa), Medium Molecular Weight ("MMW") Hyaluronan (700-1000 kDa), and High Molecular Weight ("BMW") Hyaluronan (1.0-6.0 million daltons (MDa)). In certain exemplary embodiments, the HA has a molecular weight of at least about 700 kDa, and in certain embodiments, the HA is a High Molecular Weight ("HWM") HA having a molecular weight of at least about 1 MDa. The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000 kDa or more, or any range derivable therein. It is expected that chemically modified HA's could have very different molecular weights than described above. A crosslinked HA can likewise have much higher molecular weight than noted above. Regardless, these materials are also applicable in this invention.

HA can be present in solid, lyophilized or liquid form. When in liquid form, solvents can be used to solubilize HA. Solvent can include, but are not limited to, water, saline or other salt solutions, buffer solutions such as phosphate buffered saline, histidine, lactate, succinate, glycine, and glutamate, dextrose, glycerol, as well as combinations thereof.

The concentration of HA present in the formulation can also vary, but in an exemplary embodiment HA is provided at a pharmaceutically effective amount. In one embodiment, the HA has a concentration of at least about 1 mg/ml. In an exemplary embodiment, the HA has a concentration of at least about 5 mg/ml, and more preferably at least about 7 mg/ml, and more preferably at least about 10 mg/ml, and more preferably at least about 15 mg/ml, and in some embodiments the concentration can be at least about 25 mg/ml. In another embodiment, the HA can have a concentration in the range of about 15 mg/ml to about 25 mg/ml. Suitable concentrations of HA include about 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/l, 60 mg/ml or more or any range derivable therein.

In one embodiment, the first component comprises an HA having a high molecular weight (1 to 6 MDa) having a concentration in the range of about 5-40 mg/ml. One such product is Orthovisc® manufactured by Anika Therapeutics, Inc. of Bedford, Mass. Orthovisc® is a sterile, non-pyrogenic, clear, viscoelastic solution of hyaluronan. Orthovisc® consists of high molecular weight (1.0-2.9 MDa), ultra-pure natural hyaluronan dissolved in physiological saline and having a nominal concentrations between 12.5-17.5 mg/ml. Orthovisc® is isolated through bacterial fermentation. One skilled in the art will recognize that there are companies such as Shiseido and Lifecore who can produce high molecular weight HA through a bacterial fermentation process. Another example of an HA product available in the United States with these characteristics is Euflexxa®.

Stabilizers

The HA can be combined with at least one stabilizer. Stabilizers can be used in the methods and compositions of the present invention. Stabilizers can be sugars or derivatives, such as saccharides, disaccharides, modified saccharides, sugar alcohols, or polysaccharides. In an exemplary embodiment, the stabilizer can be tocopherol, tocopherol derivatives, glucose, mannitol, sucrose and/or trehalose.

Common stabilizers or stabilizing excipients used in the pharmaceutical industry are saccharides, disaccharides, modified saccharides, sugar alcohols and polysaccharides. Some of these molecules are commonly used as excipients because they can also serve as a sweetening agent when the drug is in a tablet form for oral delivery. According to U.S. Pat. No. 7,351,798, hyaluronic acid and glycosaminoglycans can also be excipients. It has long been believed that these polysaccharides are stable molecules. In fact, all HA materials that are marketed in the US are stored at room temperature. Some of these HA products are in buffered solutions or in saline solutions but none have any other excipient included. These HA products are approved in the US as viscosupplementation devices and are injected into the joint to relieve the pain that results from osteoarthritis. In addition, a product on the market called Viscoat (sold by Alcon) is a formulation that incorporates hyaluronic acid and chondroitin sulfate in a buffered solution and contains no other excipients. This product is used in ophthalmic surgery during the implantation of intraocular lenses. It is known that storage of HA at room temperature results in gradual loss of stability and degradation to lower molecular weights, especially in the presence of other components, such as chondroitin sulfate, hence the refrigerated storage requirement for Viscoat Tocopherol belongs to a class of chemical compounds that encompass mono, di and trimethyltocols. Many of the tocopherols demonstrate vitamin E activity. Beta, gamma and delta are stereoisomers of alpha-tocopherol. Esters of tocopherol are often used in cosmetic and personal care products. These esters include, tocopheryl acetate, the acetic acid ester of tocopherol; tocopheryl linoleate, the linoleic acid ester of tocopherol; tocopheryl linoleate/oleate, a mixture of linoleic and oleic acid esters of tocopherol; tocopheryl nicotinate, the nicotinic acid ester of tocopherol; and tocopheryl succinate, the succinic acid ester of tocopherol, potassium ascorbyl tocopheryl phosphate, a salt of both vitamin E (tocopherol) and vitamin C (ascorbic acid) may also be used in cosmetic products.

Other tocopherol-derived ingredients that may be found in cosmetic products include dioleyl tocopheryl methylsilanol, which is the dioleyl ether of tocopheryl acetate monoether with methylsilanetriol, and tocophersolan, which is also called tocopheryl polyethylene glycol 1000 succinate. The addition of succinic acid and an average of 22 ethylene oxide groups to tocopheryl makes tocophersolan a water-soluble form of tocopherol.

Mannitol is also an exemplary stabilizer due to its low hygroscopicity, excellent chemical and physical drug compatibility, better sweetness and relatively slower dissolution kinetics. It also has relatively low aqueous solubility and good dispersibility and often used to enhance formulation stability where other excipients have failed. Mannitol can be used in a wide array of dosage forms, including but not limited to, tablets, capsules, sachets, pastilles, liquids, emulsions, suspensions, ointments, paste, lotions and intravenous solutions.

Mannitol also serves as a matrix forming additive for lyophilization. When used at concentrations up to 10% w/v, mannitol forms an amorphous (non-crystalline) matrix which supports proteins and other biomolecules for freeze drying. It is generally inert and once freeze dried, rehydrates rapidly. Its amorphous structure while frozen prevents it from disrupting proteins while providing channels for water sublimation during processing.

Similar to mannitol, sucrose is also widely used in tablet form for oral delivery due to its sweetness and palatability. Sucrose, is a non-reducing disaccharide (glucose linked by its anomeric carbon to fructose) that is widely used as a lyoprotectant.

Trehalose ($\alpha$-D-glucopyranosyl $\alpha$-D-glucopyranoside), a disaccharide known for its antioxidant properties, has been known as a non-reducing saccharide consisting of glucoses. As is described in Advances in Carbohydrate Chemistry, Vol. 18, pp. 201-225 (1963), published by Academic Press, USA, and Applied and Environmental Microbiology, Vol. 56, pp. 3,213-3,215 (1990), trehalose widely exists in microorganisms, mushrooms, insects, etc., though the content is relatively low. Trehalose is a non-reducing saccharide, so that it neither reacts with substances containing amino groups such as amino acids and proteins, induces the amino-carbonyl reaction, nor deteriorates amino acid-containing substances. Thus, trehalose can be used without a fear of causing an unsatisfactory browning and deterioration.

Trehalose can also inhibit the inflammatory cascade, thereby suppressing cytokine production. (Minutoli, et al, SHOCK, Vol. 27, No. 1, pp. 91-96, 2007; and Chen Q, Haddad G G: Role of trehalose phosphate synthase and trehalose during hypoxia: from flies to mammals. J Exp Biol 207:3125-3129, 2004.) Trehalose is a unique sugar capable of protecting biomolecules against environmental stress and may inhibit the inflammatory cascade that in turn causes oxidative damage and cytokines production. Trehalose has also been shown to preserve cell viability, during exposure to a range of environmental stress, such as heat shock, dehydration and hypoxia.

Trehalose is also a common food additive because it is a strong antioxidant and sweetener, and it is often used as a stabilizing agent in pharmaceutical preparations. Trehalose, like sucrose, is a non-reducing disaccharide (two glucose molecules linked by the anomeric carbon) that can act as an effective lyoprotectant for the freeze drying of proteins and other biomolecules. During the freeze drying process, proteins can denature as water is removed unless a substitute molecule is available to support the structure of the protein. Trehalose fills the void left by exiting water and prevents this denaturation. When used at concentrations as low as 2% it can effectively protect proteins and other biomolecules.

Useful forms of trehalose can include trehalose dihydrate (TD) which is crystalline, amorphous trehalose (AT) which is a vitreous form, and the anhydrous forms of trehalose, anhydrous amorphous trehalose (AAT) and anhydrous crystalline trehalose (ACT). Powdered anhydrous trehalose may contain AAT and/or ACT. The term "trehalose," as used herein, refers to any physical form of trehalose including anhydrous, partially hydrated, fully hydrated and mixtures and solutions thereof. The manufacture and use of anhydrous trehalose from TD can be found in International Publication No.: PCT/GB97/00367, the disclosure of which is incorporated into this specification by reference.

The addition of trehalose to the formulation or composition can help stabilize high molecular weight HA as well as inhibit damaging inflammatory cascades. Trehalose can be present in liquid, solid, lyophilized or crystalline forms. When present in liquid form, trehalose can be in a buffered solution. Solvents that can be used to solubilize trehalose can include, but are not limited to, water, saline or other salt solutions, buffer solutions such as phosphate buffered saline, histidine, lactate, succinate, glycine, and glutamate, dextrose, glycerol, as well as combinations thereof. Particularly, trehalose can be present in the HA formulation as a solution.

At least one stabilizer, can be present in the HA formulation. Solvents that can be used to solubilize the stabilizer can include, but are not limited to, water, saline or other salt solutions, buffer solutions such as phosphate buffered saline, histidine, lactate, succinate, glycine, and glutamate, dextrose, glycerol, as well as combinations thereof. Particularly, the stabilizer can be present in the HA formulation as a solution.

The concentration of the at least one stabilizer present in the HA formulation can vary, but in an exemplary embodiment at least one excipient is provided at a pharmaceutically effective amount. In an exemplary embodiment, the at least one stabilizer has a concentration of at least about 1 mg/ml, and more preferably at least about 5 mg/ml, and more preferably at least about 50 mg/ml, and more preferably at least about 100 mg/ml, and in some embodiments the concentration can be at least about 200 mg/ml. Suitable concentrations of at least one stabilizer can include about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 160 mg/ml, 170 mg/ml, 180 mg/ml, 190 mg/ml, 200 mg/ml, 300 mg/ml, 400 mg/ml, 500 mg/ml, 600 mg/ml or more or any range derivable therein. Stabilizers can also be in a concentration in a range of about 0.1-60% by weight; about 0.1-50% by weight, about 0.1-45% by weight; or about 0.1-20% by weight. Other suitable concentrations of at least one excipient can include about 0.1%, 0.5%, 1%, 2.5%, 5%, 6%, 7%, 8%, 9% 10%, 11%, 12%, 13%, 14%, 15%, 16%, 17%, 18%, 19%, 20%, 25%, 30%, 35%, 40%, 45%, 50%, 55%, or about 60% by weight.

Additional Components

In an exemplary embodiment, at least one additional component can also be combined with the HA formulation or composition. The additional component can be a lyophilized glycosaminoglycan (GAG) or GAG precursor. The term "glycosaminoglycan," or "GAG," refers interchangeably to the family of sulfated mucopolysaccharides that typically include heparin, heparin sulfate, chondroitin, chondroitin sulfate, keratan sulfate, dermatan sulfate, and their respective derivatives.

Glycosaminoglycans (GAGs) are long unbranched polysaccharides containing a repeating disaccharide unit. The disaccharide units contain either of two modified sugars, N-acetylgalactosamine (GalNAc) or N-acetylglucosamine (GlcNAc), and a uronic acid such as glucuronate or iduronate. GAGs are highly negatively charged molecules, with extended conformation that imparts high viscosity to the mixture. GAGs are located primarily on the surface of cells or in the extracellular matrix (ECM). Along with the high viscosity of GAGs comes low compressibility, which makes these molecules ideal for a lubricating fluid in the joints. GAGs can thus help slow down the inflammatory process. At the same time, their rigidity provides structural integrity to cells and provides passageways between cells, allowing for cell migration. In addition, a GAG such as CS has been found in the synovial fluid and may play a role in health of the joint. Therefore it can be advantageous to have a therapy that can deliver CS at the same time as HA. It is believed that CS can enhance the efficacy of HA. However, it has been observed that HA in the presence of CS can degrade over time. Therefore, in order to prevent this degradation, HA must be refrigerated until use. However, most clinics and hospitals do not have the capacity to store these types of products in a refrigerator, so it would be beneficial to provide products that combine HA and GAGs that are stable and that are capable of being stored at room temperature.

The GAGs can have various molecular weights, but in certain exemplary embodiments the molecular weight is in the range about 5 to 1,000 kDa, more preferably in the range of about 6 to 500 kDa, more preferably in the range of about 7 to 300 kDa, more preferably in the range of about 8 to 200 kDa, more preferably in the range of about 9 to 100 kDa, and most preferably in the range of about 10 to 80 kDa. In other embodiments, the molecular weight of the GAG fragment is below about 5 kDa and even more preferably below about 3 kDa.

The concentration of GAGs present in mixture can also vary, but in an exemplary embodiment the GAG is provided at a pharmaceutically effective amount. In an exemplary embodiment, the GAG has a concentration of at least about 0.1 mg/ml, and more preferably at least about 2 mg/ml, and more preferably at least about 5 mg/ml, and more preferably at least about 7 mg/ml, and more preferably at least about 20 mg/ml. In another embodiment, the GAG or GAG precursor can be present in the composition at a concentration in the range of about 0.1 mg/ml to about 20 mg/ml. Suitable concentrations of GAGs include about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml or more or any range derivable therein.

Chondroitin sulfate (CS), which is an essential component of cartilage, is composed of an alternating sequence of sulfated and/or unsulfated D-glucuronic acid (GlcA) and N-acetyl-D-galactosamine (GalNAc) residues linked through alternating $\beta(1,3)$ and $\beta(1,4)$ bonds. These compounds each have a polymeric structure consisting mainly of about 40 to 100 times repetition of the disaccharide units. CS can be used at various molecular weights and concentrations, as discussed above with respect to the GAG component, but in an exemplary embodiment, the CS has a molecular weight of in the range of about 10,000 to 80,000 kDa and a concentration in the range of about 0.1 to 100 mg/ml. CS can be isolated from bovine or marine sources. A chondroitin chain can have over 100 individual sugars, each of which can be sulfated in variable positions and quantities. Chondroitin-4 sulfate, also carbon 4 of the N-acetylgalactosamine (GalNAc) sugar, is found in nasal and tracheal cartilages of bovines and porcines. It is also found in the bones, flesh, blood, skin, umbilical cord, and urine of these animals. Chondroitin-6 sulfate, also carbon 6 of the GalNAc sugar, has been isolated from the skin, umbilical cord, and cardiac valves of these animals. Chondroitin-6 sulfate has the same composition, but slightly different physical properties from chondroitin-4 sulfate. Chondroitin sulfate is involved in the binding of collagen and is also directly involved in the retention of moisture. These are both properties that aid the healing process. A person skilled in the art will appreciate that the terms "chondroitin sulfate," "CS," "chondroitin," "chondroitin sulfuric acid," and "chonsurid" are used interchangeably herein and also encompass chemical or isomeric or cross-linked derivatives throughout this application.

Dermatan sulfate (DS), also called chondroitin sulfate B, is mainly made up disulfated and/or trisulfated disaccharide units of L-iduronic acid and N-acetyl-D-galactosamine joined by $\beta1,4$ or 1,3 linkages, but there is a case where some of the repeating units contain sulfated L-iduronic acid or D-glucuronic acid as uronic acid, or contain non-sulfated N-acetylgalactosamine or 4,6-disulfated N-acetylgalactosamine instead of N-acetylgalactosamine-4-sulfate. DS is defined as a chondroitin sulfate by the presence of GalNAc. The presence of iduronic acid (IdoA) in DS distinguishes it from chondroitin sulfates-A (4-O-sulfated) and -C (6-O-sulfated) and likens it to heparin and HS, which also contain this residue. It is considered that dermatan sulfate is absorbed by the body when orally taken. The molecular weight and concentration of DS can vary, as discussed above with respect to the GAG component, but in an exemplary embodiment the molecular weight is in the range of about 10 to 80 kDa and a concentration in the range of about 0.1-100 mg/ml. A person skilled in the art will appreciate that, unlike HA which is bacterially fermented and therefore has a molecular weight that can be controlled, dermatan sulfate is isolated from animal tissue and may contain fragments. The molecular weight of the dermatan sulfate, and any fragments contained therein, can therefore significantly vary. A person skilled in the art will also appreciate that the terms "dermatan sulfate," "DS," and "dermatan" are used interchangeably herein and also include sulfated derivatives of dermatan sulfate, the dermatan sulfate benzethonium salt, the persulfated derivatives of dermatan sulfate benzethonium salts, and also the dermatan sulfate sodium salt.

Heparin and heparan sulfate (HS) are composed of a glucuronic acid (GlcA) linked to N-acetylglucosamine. They are composed of α1-4 linked disaccharide repeating units containing a uronic acid and an amino sugar. Heparan sulfate proteoglycans are an integral part of the basement membrane. HS proteoglycan is a large biomolecule with a molecular mass as great as 400 kDa, composed of a core protein covalently bound to heparan sulfate chains. The number of the polysaccharide chains and the size of the core protein may vary according to the source. Heparan sulfate proteoglycan is a multifunctional molecule binding to fibroblast growth factors, vascular endothelial growth factor (VEGF), and VEGF receptors through the sugar moiety, acting as a docking molecule for matrilysin (MMP-7) and other matrix metalloproteinases and playing important roles in cell proliferation and differentiation. Heparan sulfate proteoglycans also promote attachment of cells by binding to a variety of molecules found in the extracellular matrix including laminin, fibronectin, collagen type IV, and FGF-basic. The molecular weight and concentration of HS can vary, as discussed above with respect to the GAG component, but in an exemplary embodiment the molecular weight is in the range of about 3-30 kDa (when isolated from tissues) and a concentration in the range of about 0.1-100 mg/ml.

Keratan sulfate, also keratosulfate (KS), is highly-negatively charged and found principally in aggrecan, the most abundant proteoglycan in the extracellular matrix of hyaline, fibrous and elastic cartilage. KS is composed of disaccharide repeating unit, -4GlcNAcβ1-3Galβ1-. Sulfation occurs at carbon position 6 (C6) of either or both the galactose (Gal) or GlcNAc. Specific KS types are composed of three regions: a linkage region, at one end of which the KS chain is linked to the core protein, the repeating disaccharide unit, and chain capping region, occurring at the opposite end of the KS chain to the protein linkage region. The molecular weight and concentration of KS can vary, as discussed above with respect to the GAG component, but in an exemplary embodiment the molecular weight is in the range of about 5-10 kDa (when isolated from tissues) and a concentration in the range of about 1-100 mg/ml.

The concentration of GAGs or GAG precursors present in mixture can also vary, but in an exemplary embodiment the GAG or GAG precursor is provided at a pharmaceutically effective amount. In an exemplary embodiment, the GAG or GAG precursor has a concentration of at least about 0.1 mg/ml, and more preferably at least about 2 mg/ml, and more preferably at least about 5 mg/ml, and more preferably at least about 7 mg/ml, and more preferably at least about 20 mg/ml. In another embodiment, the GAG or GAG precursor can be present in the composition at a concentration in the range of about 0.1 mg/ml to about 20 mg/ml. Suitable concentrations of GAGs or GAG precursors include about 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml or more or any range derivable therein.

A person skilled in the art will appreciate that, while lyophilized GAGs or GAG precursors are particularly useful in exemplary embodiments, liquid GAGs or GAG precursors can also be used in the composition. For example, CS can be obtained in powder form and mixed with a solvent, such as water, to form a solution. The solution can be combined with liquid HA to form a mixture having a reduced viscosity, as compared to the HA alone. While effective to reduce the viscosity of the HA, the resulting mixture will have a reduced concentration due to the presence of water. Thus, while liquid, non-lyophilized GAGs can be used with the present invention, in an exemplary embodiment the GAG is lyophilized to allow for the use of HA at a high concentration.

Glucosamine ($C_6H_{13}NO_5$) ("GlcN") or its derivatives or other GAG precursors can also be included in the HA formulation to enhance synthesis of key components of cartilage and synovial fluid by feeding both reactions necessary for the production of hyaluronan as well as for proteoglycans. GlcN is an amino sugar carrying four hydroxyl groups and an amine group, and it is a prominent precursor in the biochemical synthesis of glycosylated proteins and lipids. GlcN is a naturally occurring molecule that has nutritive and effector functions. For example, GlcN is compatible with and promotes stem cell growth and differentiation of mesenchymal stem cells to form chondrocytes. GlcN can have a role in tissue development and repair, such as cartilage growth and development, in general. It is used as a nutritional supplement to combat the symptoms of OA, and has been shown slow cartilage destruction in clinical studies. In one embodiment, the GlcN can by lyophilized together with the CS. Salt forms of glucosamine can have limited stability in liquid phase. In addition, HCl salt of GlcN can lower the pH sufficiently to degrade the HA once combined. For this reason, in order to retain stability of the components, it is advantageous to have GlcN in the lyophilized form to be solubilized with HA gel prior to injection. As used herein, "glucosamine" includes glucosamine salts, such as glucosamine hydrochloride and glucosamine sulfate, as well as non-salt forms such as N-acetylglucosamine.

The concentration of the GlcN can vary. A suitable local concentration can be at least about 10 mg/ml, about 9 mg/ml, about 8 mg/ml, about 7 mg/ml, about 6 mg/ml, 5 mg/ml, 4.5 mg/ml, 4 mg/ml, 3.5 mg/ml, 3 mg/ml, about 2.9 mg/ml, about 2.8 mg/ml, about 2.7 mg/ml, about 2.6 mg/ml, about 2.5 mg/ml, about 2.4 mg/ml, about 2.3 mg/ml, about 2.2 mg/ml, about 2.1 mg/ml, about 2.0 mg/ml, about 1.9 mg/ml, about 1.8 mg/ml, about 1.7 mg/ml, about 1.6 mg/ml, about 1.5 mg/ml, about 1.4 mg/ml, about 1.3 mg/ml, about 1.2 mg/ml, about 1.1 mg/ml, about 1.0 mg/ml, about 0.9 mg/ml, about 0.8 mg/ml, about 0.7 mg/ml, about 0.6 mg/ml, about 0.5 mg/ml or so on. A person skilled in the art can determine a suitable local concentration of GlcN practicing methods known in the pharmaceutics art, and that determination will govern the nature and composition of the GlcN composition of interest to obtain the desired concentration of GlcN.

Buffering agents can also be added to the HA formulation to control pH. Examples of buffering agents can be any one or more of the following agents, and is not limited to, acetic acid, ammonium carbonate, ammonium phosphate, boric acid, citric acid, glycine, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, TRIS and sodium carbonate.

Additionally, isotonic agents can be added to control ionic concentration and/or osmotic pressure of the HA formulation. Examples of isotonic agents can be any one or more of the following agents, and is not limited to, dextrose, sucrose, trehalose, glycerin, mannitol, potassium chloride, sodium chloride.

A person skilled in the art will appreciate that the compositions and methods of the present invention can include various other joint treatment components, including, for example, amino acids, proteins, saccharides, di-saccharides, poly-saccharides, lipids, nucleic acids, buffers, surfactants, and mixtures thereof. Other useful components can include steroids, anti-inflammatory agents, non-steroidal anti-inflammatory agents, analgesics, cells, antibiotics, antimicrobial agents, anti-inflammatory agents, growth factors, growth factor fragments, small-molecule wound healing stimulants, hormones, cytokines, peptides, antibodies, enzymes, isolated cells, platelets, immunosuppressants, nucleic acids, cell types, viruses, virus particles, essential nutrients or vitamins, and combinations thereof.

Lyophilization

Any one or more of the components present in the compositions and methods of the present invention can be lyophilized using various techniques known in the art. Lyophilization is a dehydration process that is typically used to preserve a perishable material, and it works by freezing the material and then reducing the surrounding pressure and adding enough heat to allow the frozen water in the material to sublime directly from the solid phase to the gas phase. Standard lyophilization techniques known in the art can be used to lyophilize any one or more of the components. In an exemplary embodiment, the HA is lyophilized.

Prior to lyophilization, various solvents can be used to form an aqueous mixture containing the component(s) to be lyophilized. In an exemplary embodiment, the aqueous mixture is prepared by combining water with one or more of the components. In an exemplary embodiment, the composition is filter sterilized, such as with a 0.2 μm filter, prior to lyophilization.

In one embodiment, the component(s) can be lyophilized using the following cycle:

Freezing: from ambient temperature to 5° C. in 15 minutes
Hold at 5° C. for 100 minutes
Down to −45° C. in 50 minutes
Hold at −45° C. for 180 minutes
Primary Drying: set pressure at 50 mTorr
Shelf Up to −15° C. in 175 minutes
Hold at −15° C. for 2300 minutes
Secondary Drying: set pressure at 75 mTorr
Shelf Up to 25° C. in 200 minutes
Hold for 900 minutes
Cycle end: backfill with nitrogen to ~730 Torr
Capping and crimping Variations to the temperatures, times and settings can be made in accordance to practices used by a person of skilled in the art. Variations may include, but are not limited to, cycling temperatures for the freezing cycle, drying temperatures and end cycles. Variations may also include differences in holding times for the freezing, drying and capping/crimping cycles. Variations may also include differences in set pressures for the drying cycles and capping/crimping cycles. In addition, the number of drying cycles may be increased or decreased depending the machine used or component(s) to be lyophilized.

The addition of a buffering agent can provide for improved solubility and stability of the protein in lyophilized HA formulations. Biocompatible buffering agents known in the art can be used, such as glycine; sodium, potassium, or calcium salts of acetate; sodium, potassium, or calcium salts of citrate; sodium, potassium, or calcium salts of lactate; sodium or potassium salts of phosphate, including mono-basic phosphate, di-basic phosphate, tri-basic phosphate and mixtures thereof. The buffering agents can additionally have sugar added to the composition to function as a bulking agent. The pH preferably can be controlled to be between pH5 and pH10, and more preferably between pH 6 to 8.

Formulations

In one embodiment, the HA and at least one additional component, such as an excipient, can be configured to be combined and administered intra-articularly as part of a surgical procedure involving an articulating joint, either immediately before, during or immediately after the surgical procedure. Alternatively, the HA and at least one additional component could be previously combined and present as a combination formulation at the time of the surgical procedure. The other components, when combined, can form a resulting composition or mixture having each component present in the composition at various amounts. The amount of each component in the composition can vary, but in an exemplary embodiment, the mixing ratio between HA and at least one additional component, such as an excipient, can have a weight ratio of HA to additional component in the range of about 1:0.001 to about 1:100, and more preferably at a ratio in the range of about 1:0.01 to about 1:10. Alternatively, the formulation can include about 1% to about 75% or more by weight of each of the individual components, such as HA and at least one additional component (e.g. an excipient), in the total composition, alternatively about 2.5%, 5%, 10%, 20%, 30%, 40%, 50%, 60%, 70% or more by weight of HA and at least one additional component, such as an excipient, in the total formulation. In an exemplary embodiment, the amount of HA present in the disclosed formulation can be about 1-20% by weight of the total formulation, and the amount of at least one additional component, such as an excipient, can be present in the disclosed formulation at about 0.01-20% by weight of the total formulation.

Solvents that can be used to solubilize one or more of the components include, for example, water, acidic solvents, hydrochloric acid, acetic acid, benzoic acid, phosphate buffered saline, dextrose, glycerol, ethanol and the like, as well as combinations thereof. Solvents that can be used to solubilize HA and/or the additional component can include, but are not limited to, water, saline or other salt solutions, buffer solutions such as phosphate buffered saline, histidine, lactate, succinate, glycine and glutamate, dextrose, glycerol, hydrochloric acid, acetic acid, benzoic acid, acidic solvent and other suitable solvents, as well as combinations thereof. The formulation can also include other components, such as dispersion media, coatings, antibacterial and antifungal agents, isotonic and absorption delaying agents, and the like that are physiologically compatible. Isotonic agents include, for example, sugars, polyalcohols such as mannitol, sorbitol, or sodium chloride in the composition. The formulation can also include minor amounts of auxiliary substances such as wetting or emulsifying agents, preservatives or buffers, which enhance the shelf life or effectiveness of the formulation.

The formulations can be incorporated into pharmaceutical compositions suitable for administration to a subject. Typically, the pharmaceutical composition comprises HA and another component, such as at least one excipient, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, hydrochloric acid, acetic acid, benzoic acid, acidic solvent, saline, phosphate buffered saline, dextrose, glycerol, ethanol and the like, as well as combinations thereof. In many cases, it can be useful to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the composition.

The compositions can be in a variety of forms. These include, for example, liquid, semi-solid and solid dosage forms, such as liquid solutions (e.g., injectable and infusible solutions), dispersions or suspensions, tablets, pills, and powders. An exemplary form can depend on the intended mode of administration and therapeutic application. Typical compositions can be in the form of injectable or infusible solutions, such as compositions similar to those used for in vivo injection. In one embodiment, an exemplary mode of administration is parenteral (e.g., intra-articular, subcutaneous, intraperitoneal, intramuscular). In another embodiment, the composition can be administered by infusion or injection directly into the target area, such as a joint. In yet another embodiment, the composition can be administered by intramuscular or subcutaneous injection.

Sterile injectable solutions can be prepared by incorporating the active compound in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the embodiments can include methods of preparation of vacuum drying and freeze-drying which yields a powder of the active ingredient plus any additional desired ingredient from a previously sterile-filtered solution thereof.

Delivery Systems

The methods and compositions encompass kits for treating articular disorders, such as joints. The kits can comprise HA, and at least one stabilizer. Both and/or all the components can be housed in a single chamber. The kit can also include HA with at least one stabilizer and an additional component. The additional component can be housed in a single or separate chamber of a syringe for injecting with the HA mixture of HA and at least one stabilizer. The HA and at least one stabilizer can be lyophilized. In one exemplary embodiment, the HA is combined with at least one stabilizer in a single chamber. In another embodiment, a kit is provided having HA and the at least one stabilizer housed in the same chamber and an additional component in a second chamber. In another exemplary embodiment, the HA is combined with at least one stabilizer in the same chamber and a GAG or GAG precursor is housed in a second chamber. The HA component can comprise up to about 10 ml of Orthovisc®, which contains about 150 mg of hyaluronan, 90 mg of sodium chloride, and up to about 10.0 mL of water for injection and can be scaled appropriately for the specific indication. Examples can be for the knee, shoulder and hip, the volume of injection for a single injection product can be in the range of about 3 ml to 10 ml and the hand can be in the range of about 500 µl and 1.5 ml. The HA can have a molecular weight in the range of about 1.0 to 6 MDa. The at least one stabilizer present in the HA formulation or composition can have a concentration in the range from about 0.1 mg/ml to about 200 mg/ml. The at least one stabilizer can be lyophilized or, alternatively can be in a solution, as noted above, in combination with the HA component.

Compounds can be stored separately to increase shelf-life. The individual compounds can be lyophilized or in solid form in one syringe/cartridge with diluent or a second compound in a second syringe/cartridge. In one embodiment, one of the compounds is in lyophilized form or in solid form and the second compound is a solution capable of combining with the lyophilized/solid compound. An example can be at least one lyophilized or solid component can be stored in a first chamber and a solubilized HA can be stored in a second chamber. In another embodiment, both compounds can be lyophilized or in solid form and housed in a single or separate chambers of a syringe/cartridge. In another embodiment, compounds can be lyophilized directly in the syringe or cartridge.

Pre-filled dual-chamber syringes and/or cartridges can also be utilized with the components and compositions. Pre-filled dual-chamber syringes enable the sequential administration of two separate compositions with a single syringe push, thereby replacing two syringes with one. The benefits of a single delivery capability include increasing the speed and ease of drug administration; reducing risk of infection by reducing the number of connections; lowering the risk of drug administration or sequence errors, and quicker delivery of compositions requiring combination prior to administration. The dual-chamber syringe can accommodate lyophilized, powder or liquid formulations in the front chamber combined with diluents, saline or buffer in the rear chamber.

Prefilled syringes can contain the exact deliverable dose of desired compounds and diluents. The prefilled syringes can contain volumes from about 0.1 ml, 0.2 ml, 0.3 ml, 0.4 ml, 0.5 ml, 0.6 ml, 0.7 ml, 0.8 ml, 0.9 ml, 1.0 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, 10 ml or more or any derivative therein.

The dual syringe and/or cartridge can be side-by-side chambers with separate syringe plungers that mix into a single chamber or linear chambers with one plunger. The dual chamber syringe and/or cartridges can also have a stopper or connector in the middle to serve as a barrier between the two chambers. The stopper or connector can be removed to allow mixing or combining of the compounds in the two chambers.

FIG. 1 illustrates one embodiment of a mixing and delivery system that is in the form of a dual chamber syringe 10. As shown, the dual chamber syringe 10 generally includes a housing having proximal and distal chambers 14, 12 separated by a valve 16. A plunger 18 is slidably disposed within the proximal chamber 14 and is configured to inject fluid present within the proximal chamber 14 into the distal chamber 12 to thereby mix the components. In one embodiment, the first component, e.g., liquid HA with at least one stabilizer, can be present in the proximal chamber 14 and an additional component, e.g., one or more additional components, can be present in the distal chamber 12. Alternatively, the first component, e.g., liquid HA, can be present in the proximal chamber 14 with at least one stabilizer, such as trehalose, and at least one additional component, e.g., chondroitin sulfate, can be present in the distal chamber 12. The plunger 18 can be advanced through the proximal chamber 14 to inject the first component, e.g., liquid HA with at least one stabilizer, into the distal chamber 12 containing the second component, e.g., one or more additional components. In another embodiment, the proximal chamber 14 can contain a solvent, such as water or saline, and the distal chamber 12 can contain all of the components in solid form. For example, the distal chamber 12 can contain lyophilized or solid HA with at least one stabilizer. The plunger 18 can be advanced through the proximal chamber 14 to inject the solvent into the distal chamber 12, thereby solubilizing the components in the distal chamber 12. Once all components are combined in the distal chamber 12, the mixture can be delivered to tissue, for example by attaching a needle to the distal end of the dual chamber syringe.

Figure 2:
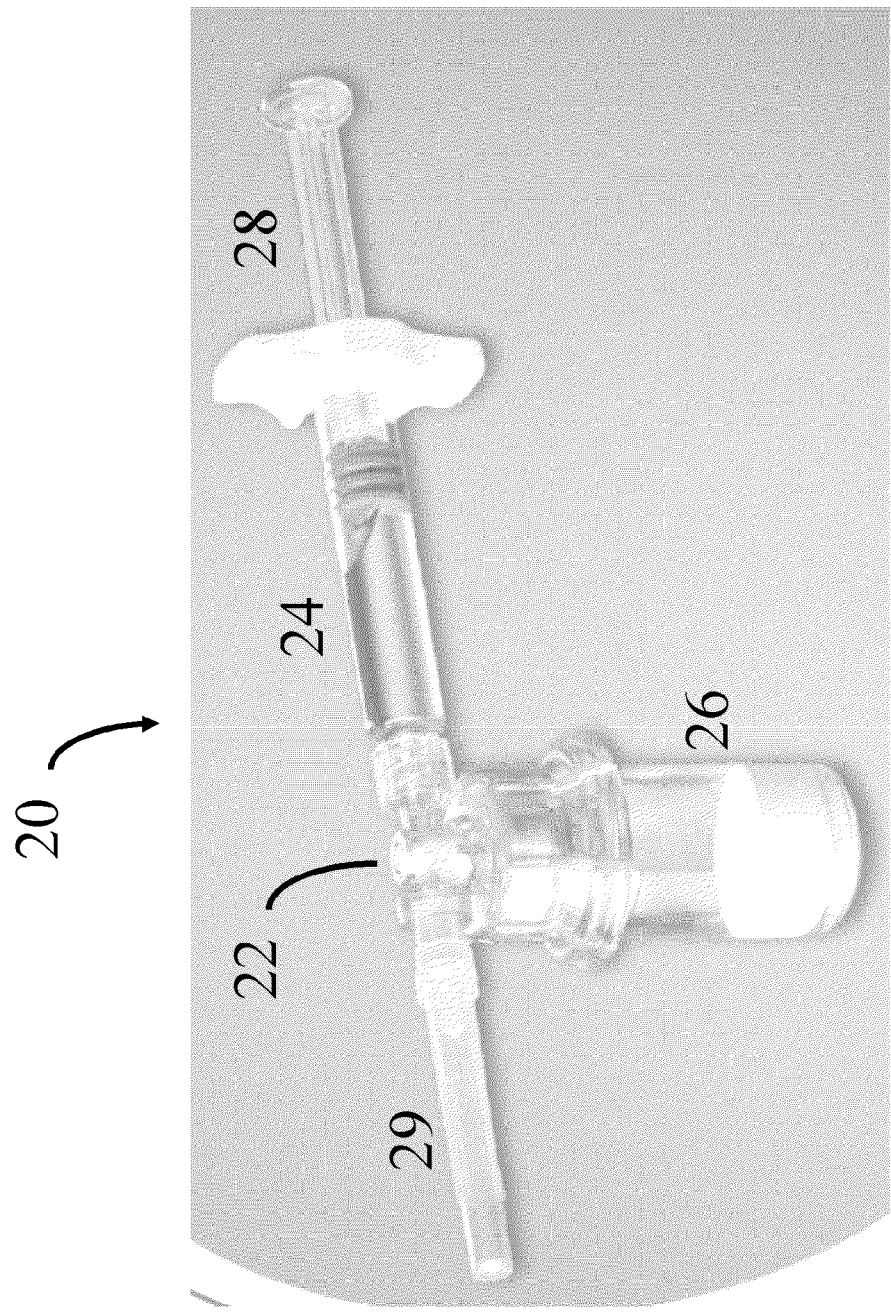
FIG. 2 is a perspective view of another embodiment of a mixing and delivery system for use with the compositions and methods of the present invention.

FIG. 2 illustrates another embodiment of a mixing and delivery system 20, which is sold commercially under the trade name MixJect®. In this embodiment, the system includes a fluid control assembly 22 that is coupled between a syringe 24 and a vial 26. The syringe 24 defines a first chamber 24a (not labeled in figure) which can contain a liquid, such as liquid HA or a solvent, and the vial defines a second chamber 26a (not labeled on figure) which can contain a solid, such as one or more additional components. Deployment of the plunger 28 through the syringe 24 will inject the liquid through the control system and into the vial 26, where the solid will be solubilized by the liquid. Once the components are fully solubilized, the vial 26 can be inverted and the plunger 28 can be retracted to draw the mixture back into the chamber 24a in the syringe 24. The vial 26 can then be removed from the system, and the mixture can be injected from the syringe through a needle 29 and into tissue.

A person skilled in the art will appreciate that any dual chamber systems known in the art can be used, and that the chambers can be side-by-side chambers with separate syringe plungers that mix into a single chamber or linear chambers with a single plunger.

Treatments

The method and compositions can be administered, for in vivo applications, parenterally by injection or by gradual perfusion over time. Administration may be intraarticular, intravenous, intraperitoneal, intramuscular, subcutaneous, intracavity, or transdermal. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

Frequently used "carriers" or "auxiliaries" include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols, and dimethyl sulfoxide. Intravenous vehicles include fluid and nutrient replenishers. Preservatives include antimicrobial agents, antioxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co.: 1405-1412, 1461-1487, 1975 and The National Formulary XIV., 14th ed. Washington: American Pharmaceutical Association, 1975 the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

Examples of symptoms or diseases, for which the composition and methods disclosed herein can be useful, encompass treating articular disorders, such as arthritis caused by infections, injuries, allergies, metabolic disorders, etc., rheumatoids such as chronic rheumatoid arthritis, and systemic lupus erythematosus; articular disorders accompanied by gout, arthropathy such as osteoarthritis, internal derangement, hydrarthrosis, stiff neck, lumbago, etc. Varying the effects depending on the use of the composition or the types of diseases to be treated, the agent can exert desired prophylactic and alleviative effects, or even therapeutic effects on swelling, pain, inflammation, and destroying of articulations without seriously affecting living bodies. The composition for treating articular disorder can be used to prevent the onset of articulation disorders, as well as to improve, alleviate, and cure the symptoms after their onsets.

The methods of treatment can include directly injecting the compositions into the target area, such as a joint. Injections can be performed as often as daily, weekly, several times a week, bi monthly, several times a month, monthly, or as often as needed as to provide relief of symptoms. For intra-articular use, from about 1 to about 30 mg/ml of HA per joint, depending on the size of the joint and severity of the condition, can be injected. The frequency of subsequent injections into a given joint are spaced to the time of recurrence of symptoms in the joint. Illustratively, dosage levels in humans of the composition can be: knee, about 1 to about 30 mg/ml per joint injection; shoulder, about 1 to about 30 mg/ml of HA per joint injection; metacorpal or proximal intraphalangeal, about 1 mg/ml to about 30 mg/ml of HA per joint injection; and elbow, about 1 to about 30 mg/ml per joint injection. The total amount of injection can range from about 1 mg/ml to 200 mg/ml of HA.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy. The pharmaceutical compositions can be prepared and administered in dose units. Under certain circumstances, however, higher or lower dose units may be appropriate. The administration of the dose unit can be carried out both by single administration of the composition or administration can be performed in several smaller dose units and also by multiple administrations of subdivided doses at specific intervals.

In one embodiment, the medical condition is osteoarthritis (OA) and the composition is administered in a joint space, such as, for example, a knee, shoulder, temporo-mandibular and carpo-metacarpal joints, elbow, hip, wrist, ankle, and lumbar zygapophysial (facet) joints in the spine. The viscosupplementation may be accomplished via a single injection or multiple intraarticular injections administered over a period of weeks into the knee or other afflicted joints. For example, a human subject with knee OA may receive one, two, three, four, or five injections of about 0.5, 1, 1.5, 2, 3, 4, 5, 6, 7, 8, 9, 10 ml or more per knee. For other joints, the administered volume can be adjusted based on the size on the joint.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

EXPERIMENTAL DATA

Example 1

Stability of Liquid HA and CS Formulations with Various Stabilizers

Figure 3:
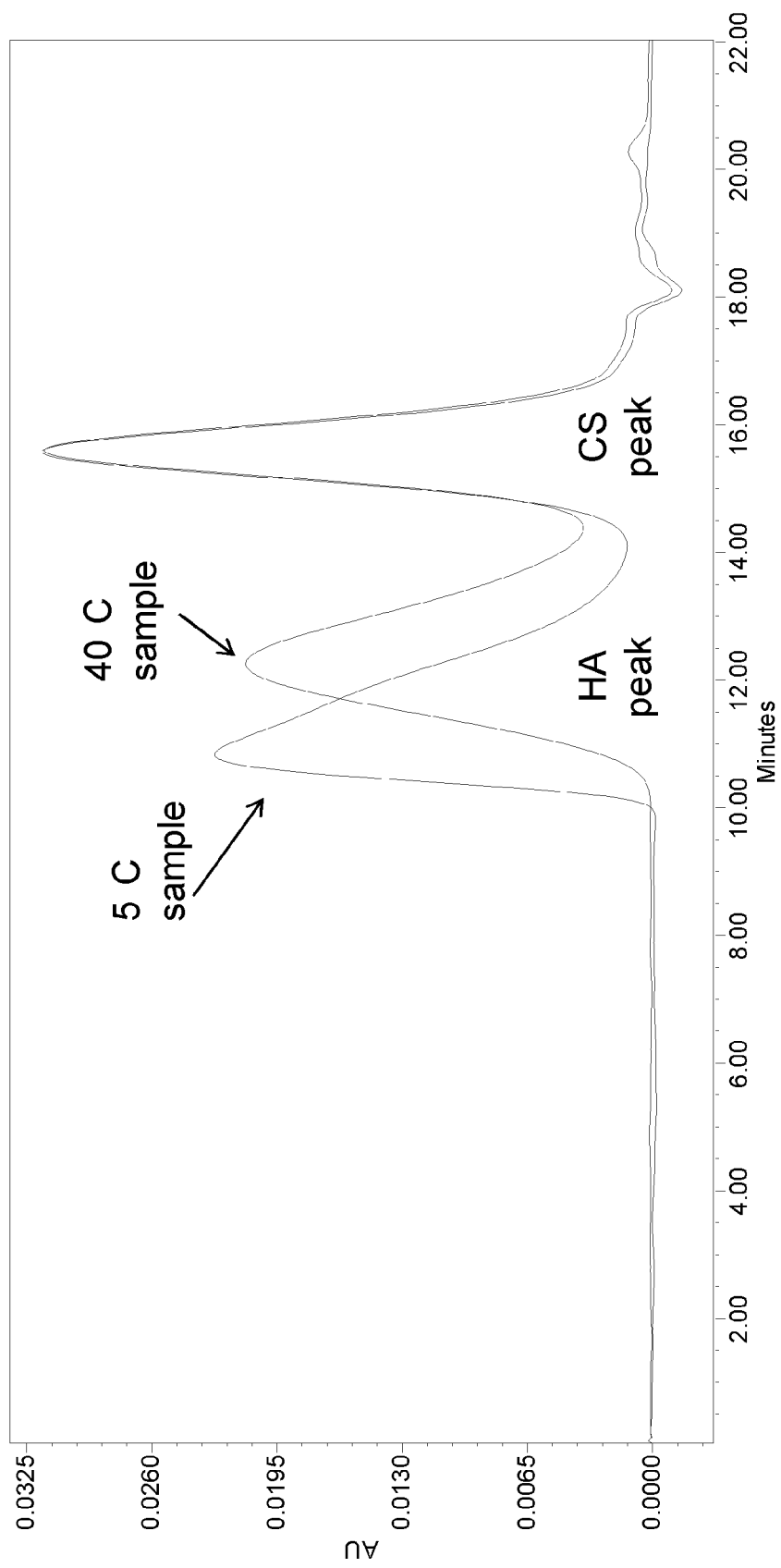
FIG. 3 shows the degradation of HA as determined by size exclusion chromatography-high performance liquid chromatography (SEC-HPLC) when in a HA and CS saline solution stored at 5° C. and 40° C./75% RH for 5 months.

HA at 2.5 mg/mL and Chondroitin sulfate (CS) at 2.5 mg/mL were formulated with different stabilizers as outlined in Table 1. The formulations were tested for HA stability at 5° C. and 40° C./75% RH storage conditions (FIG. 3). After five months, the test samples were analyzed by a size exclusion chromatography (SEC)-high performance liquid chromatography method. Briefly, the test sample was diluted with a mobile phase (100 mM sodium phosphate buffer, pH 7) to 0.1 mg/mL HA. The diluted sample was then injected onto a HPLC column (phenomenex, Poly Sep-GFC-P linear column, catalog number 00H-3147-KO) with a flow rate of 0.6 mL/min. The eluted HA peaks were monitored with 207 nm wavelength and the retention time was compared with HA molecular weight standards to determine the molecular weight of the test sample.

Figure 4:
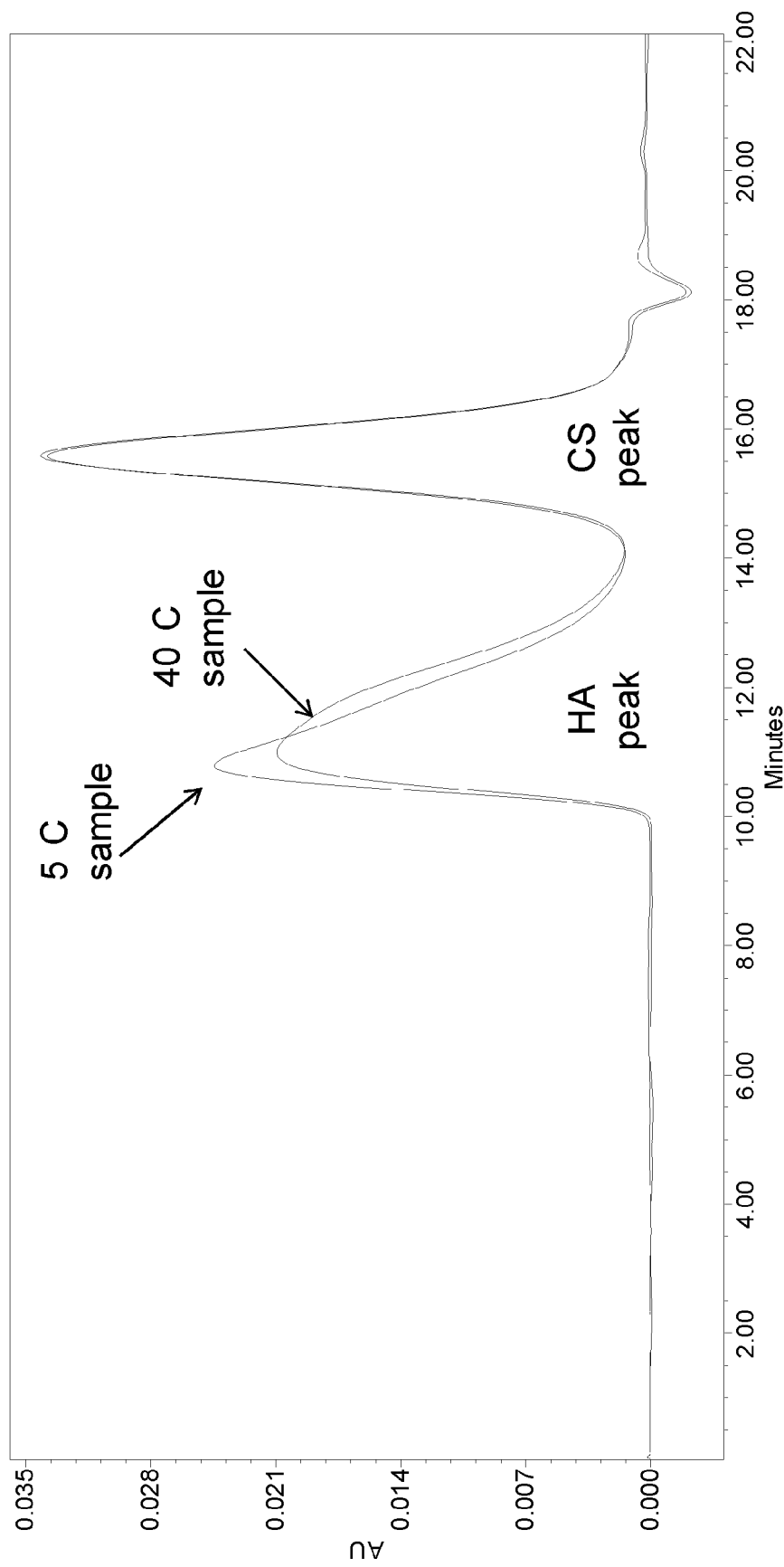
FIG. 4 shows the stabilizing effect trehalose has on HA when in solution with CS stored at 5° C. and 40° C./75% RH for 5 months as determined by SEC-HPLC.

As shown in Table 1, the saline formulation was the least stable formulation at 40° C. as compared to the other 40° C. samples. FIG. 3 show the chromatograms of the saline formulation. The HA peak of the saline sample shifted a lot to the right, indicating HA degraded to smaller molecules. In contrast, the 40° C. trehalose formulation had a much smaller shift as shown in FIG. 4. Similar results were observed with the sucrose and mannitol formulations. These formulations should have better shelf-life at ambient temperature as compared to the saline formulation.

TABLE 1

Stability Study of Liquid HA and CS Formulation at five month time point

| Excipients and concentration | Sample ID | Molecular weight, Dalton |
|---|---|---|
| Fresh prepared in mobile phase | Standard | 2014438 |
| 0.9% 9 (w/v) NaCl in water | Saline formulation, 5° C. | 2000484 |
| | Saline formulation, 40° C. | 487429 |
| 0.9% (w/v) NaCl with 3 mM phosphate buffer, pH 7 | PBS formulation, 5° C. | 1984656 |
| | PBS formulation, 40° C. | 783509 |
| 5% (w/v) glucose with 3 mM phosphate buffer, pH 7 | Glucose formulation, 5° C. | 2034540 |
| | Glucose formulation, 40° C. | 511731 |
| 5% (w/v) mannitol with 3 mM phosphate buffer, pH 7 | Mannitol formulation, 5° C. | 2030504 |
| | Mannitol formulation, 40° C. | 1765220 |
| 10% (w/v) sucrose with 3 mM phosphate buffer, pH 7 | Sucrose formulation, 5° C. | 2024464 |
| | Sucrose formulation, 40° C. | 1688080 |
| 10% (w/v) trehalose with 3 mM phosphate buffer, pH 7 | Trehalose formulation, 5° C. | 2089824 |
| | Trehalose formulation, 40° C. | 1706619 |
| 5% (w/v) mannitol in water | Mannitol, no phosphate formulation, 5° C. | 2112776 |
| | Mannitol, no phosphate formulation, 40° C. | 734536 |

HA at 8 mg/mL and Chondroitin sulfate at 8 mg/mL were also formulated with various stabilizers as outlined in Table 2. The formulated solutions were filled into 3-mL glass vials at 0.5 mL/vial and lyophilized. The dried samples were placed at 40° C./75% RH for stability study. After 4 months, the test samples were reconstituted with WFI and analyzed by the SEC-HPLC method as mentioned in Example 1. As shown in Table 2, the formulations containing saline had less stability as compared to the formulations containing glucose, mannitol, sucrose and trehalose. Actually no significant changes in molecular weight were detected in these lyophilized formulations when stored at 40° C. for four months.

TABLE 2

Stability of Lyophilized HA and CS Formulation at four month time point

| Excipients and concentrations Pre-lyophilization | Sample ID | Molecular weight kDa |
|---|---|---|
| 0.9% (w/v) saline with 3 mM phosphate buffer, pH 7 | PBS formulation A, 40° C. | 873 869 |
| 5% (w/v) glucose with 3 mM phosphate buffer, pH 7 | Glucose formulation B, 40° C. | 2070 2191 |
| 5% (w/v) mannitol with 3 mM phosphate buffer, pH 7 | Mannitol formulation C, 40° C. | 2020 2028 |
| 2.5% (w/v) mannitol/5% (w/v) sucrose with 3 mM phosphate buffer, pH 7 | Mannitol/sucrose formulation D, 40° C. | 2034 2046 |
| 10% (w/v) trehalose with 3 mM phosphate buffer, pH 7 | Trehalose formulation E, 40° C. | 1939 1968 |
| 10% (w/v) sucrose with 3 mM phosphate buffer, pH 7 | Sucrose formulation F, 40° C. | 2036 2024 |
| 10% trehalose with 10 mM histidine buffer, pH 7 | Trehalose formulation G, 40° C. | 1962 1960 |
| 0.9% saline in water | Saline formulation H, 40° C. | 964 978 |

High concentrations of HA were also tested. HA at 20 mg/mL and CS at 20 mg/mL formulated with various stabilizers. The formulations were tested for stability at 5° C. and 40° C./75% RH storage conditions as outlined in Table 3. After three months, the test samples were analyzed using the SEC-HPLC method. As shown in Table 3, the formulation containing saline only had less stability as compared to the formulations containing trehalose, sucrose and mannitol.

TABLE 3

Stability of liquid high concentration HA and CS formulations at three month time point

| Excipients and concentrations | Sample ID | HA MW, kDa |
|---|---|---|
| Fresh in mobile phase | std | 2077 |
| 10% (w/v) trehalose with 3 mM phosphate buffer, pH 7 | Trehalose formulation A, 5° C. formulation A, 40° C. | 2041 1565 |
| 10% (w/v) sucrose with 3 mM phosphate buffer, pH 7 | Sucrose formulation B, 5° C. formulation B, 40° C. | 2039 1590 |
| 5% (w/v) mannitol with 3 mM phosphate buffer, pH 7 | Mannitol formulation C, 5° C. formulation C, 40° C. | 1965 1611 |
| 0.9% (w/v) saline in water | Saline formulation D, 5° C. formulation D, 40° C. | 1967 785 |
| 5% (w/v) trehalose/0.23% (w/v) saline with 3 mM phosphate buffer, pH 7 | Trehalose/PBS formulation, 5 C. Trehalose/PBS formulation, 40 C. | 2023 1852 |

Example 2

Stability of HA Formulation with Various Concentrations of Trehalose

HA at different concentrations was formulated with various concentrations of trehalose as outlined in Table 4. Some of the formulated solutions were divided into two groups. One was placed at stability chambers for liquid stability study and the other was lyophilized for solid stability assessment. After three months of storage at 5° C. and 40° C./75% RH, the test samples were analyzed using the SEC-HPLC method. As shown in Table 4, no significant differences in molecular weight were observed among the samples with different concentrations of trehalose. However, without any excipients HA formulated with water only was much less stable in liquid form and lyophilized form.

TABLE 4

Stability of HA formulation with various concentrations of trehalose

| Formulation composition | Formulation ID | Molecular Weight kDa |
|---|---|---|
| 10 mg/mL HA with 5% (w/v) trehalose in water | Liquid 177A, 5° C. | 2103 |
|  | Liquid 177A, 40° C. | 1902 |
| 2 mg/mL HA with 2% (w/v) trehalose in water | Liquid 146A, 5° C. | 2050 |
|  | Liquid 146A, 40° C. | 1713 |
|  | Lyo 146A, 5° C. | 2090 |
|  | Lyo 146A, 40° C. | 2036 |
| 2 mg/mL HA with 0.67% (w/v) trehalose in wter | Liquid 146B, 5° C. | 2052 |
|  | Liquid 146B, 40° C. | 1690 |
|  | Lyo 146B, 5° C. | 2112 |
|  | Lyo 146B, 40° C. | 2013 |
| No any excipients | Liquid 171E, 5° C. | 2057 |
|  | Liquid 171D, 40° C. | 666 |
|  | Lyo 171E, 5° C. | 2038 |
|  | Lyo 171E, 40° C. | 731 |

Example 3

Rat MMT Model of Osteoarthritis

In the rat medial mensical tear (MMT) model of osteoarthritis, transection of the medial meniscus results in joint deterioration and reduced weight bearing that mimics human osteoarthritis. A unilateral medial meniscal tear in 300-400 gram rats results in rapidly progressive cartilage degenerative changes characterized by chondrocyte and proteoglycan loss, fibrillation, osteophyte formation and chondrocyte cloning. Such changes are typically observed to be substantial by day 21 following the meniscal surgery. The extent of joint deterioration, as determined primarily by the extent of cartilage lesions formed, can be measured using a semi-quantitative histological scoring system.

To test the utility of trehalose as a vehicle for intra-articularly injected compounds, a solution of trehalose was formulated as a 5% solution in 3 mM glycine-HCl buffer, having a pH of approximately 3. The solution was tested in the rat MMT model. Transection of the medial collateral ligament just below attachment to the meniscus was performed on 15 male Lewis rats. The meniscus was cut at its narrowest point (away from the ossicles) taking care not to damage the tibial surface.

Beginning three days after MMT surgery, intra-articular injections of the trehalose solution were given weekly for five weeks, followed by euthanasia at week six.

Figure 5:
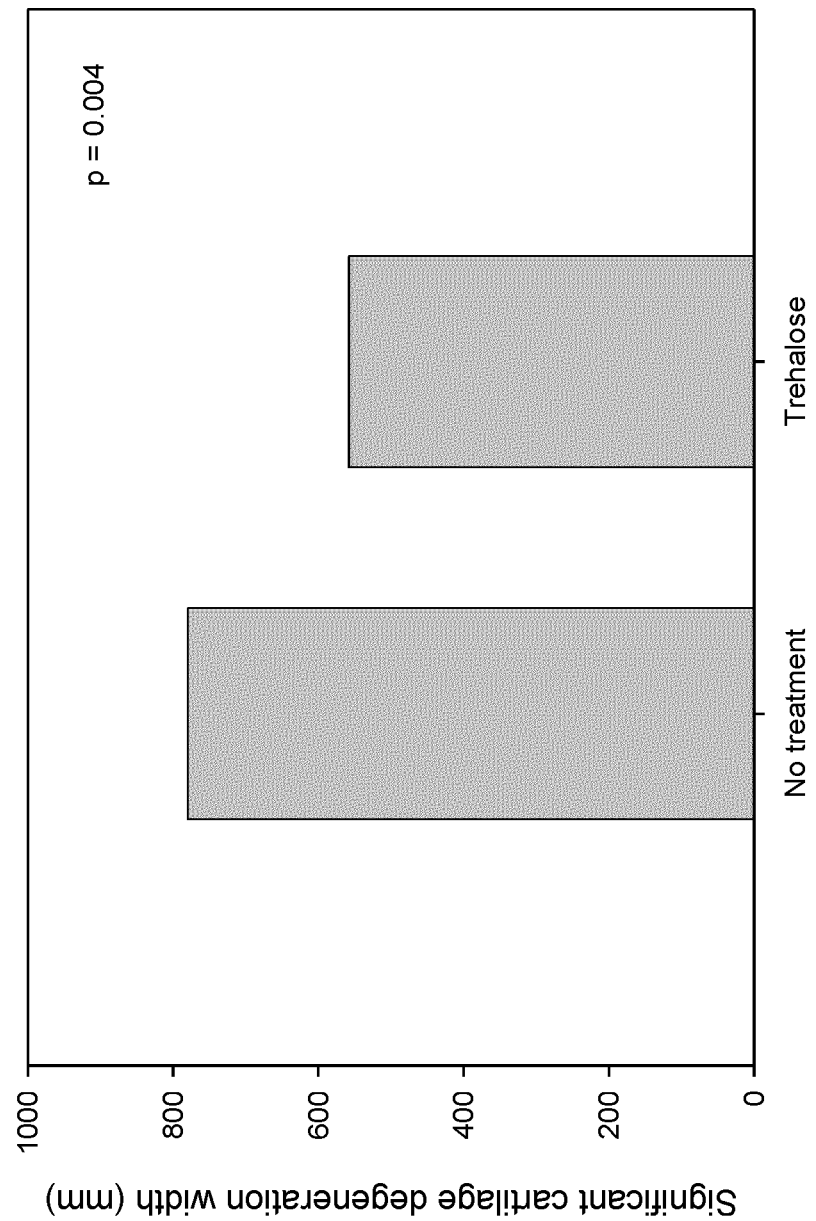
FIG. 5 is a graph comparing cartilage lesion widths in a rat medial meniscal tear (MMT) model that received intra-articular injections of trehalose to those that received no treatment.

Histology results showed that the trehalose solution gave an unexpected improvement in cartilage preservation. As shown in FIG. 5, trehalose gave a significant reduction in the width of significant cartilage lesions, as defined by the width of tibial cartilage lesions in which chondrocyte and proteoglycan loss extend through 50% or more of the original cartilage thickness. Such measurements are taken using an ocular micrometer from stained histological cross sections of the medial compartment of the joint.

Figure 6:
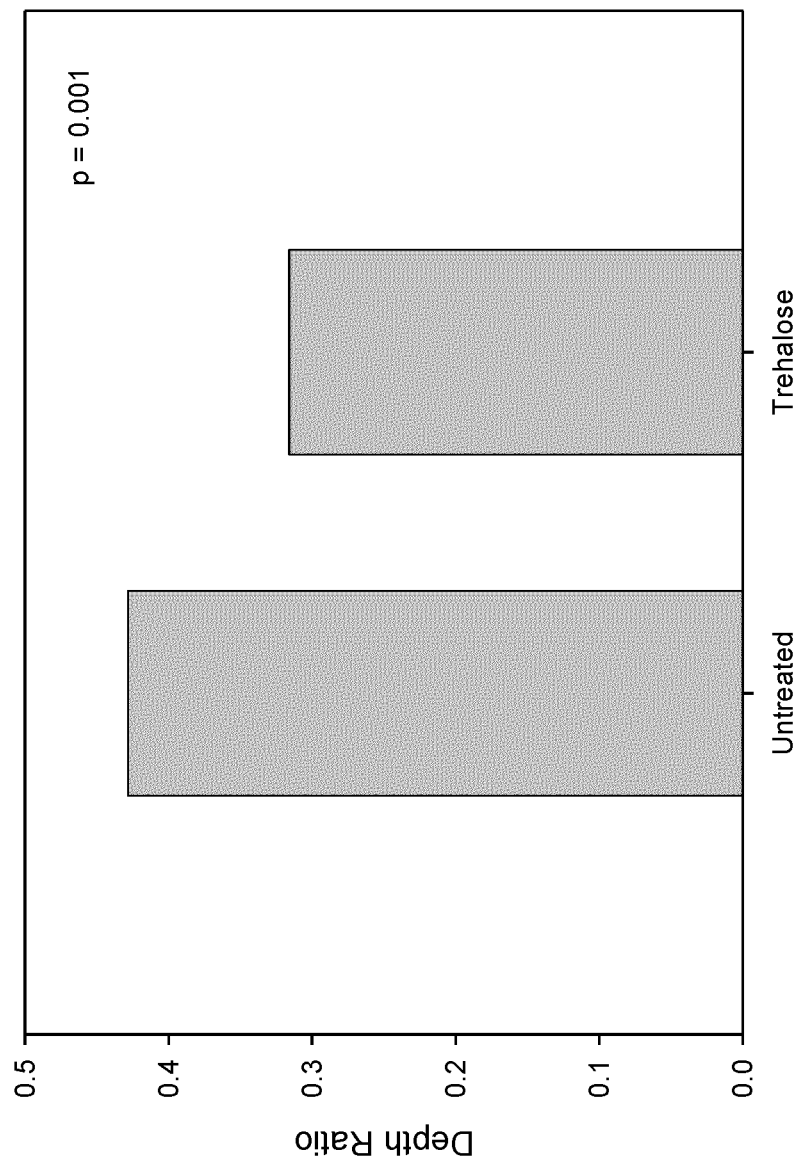
FIG. 6 is a graph comparing cartilage lesion depth ratio in the rat MMT model that received the intra-articular injections of trehalose to those that received no treatment.

Another measure of cartilage preservation is shown in FIG. 6. Trehalose demonstrated significant improvement in lesion Depth Ratio, which is calculated by comparing the depth of the lesion with the original cartilage thickness, which is estimated by measuring the distance from the extrapolated original tibial plateau to the tidemark. These measurements are taken using an ocular micrometer from stained histological cross sections of the medial compartment of the joint.

Figure 7:
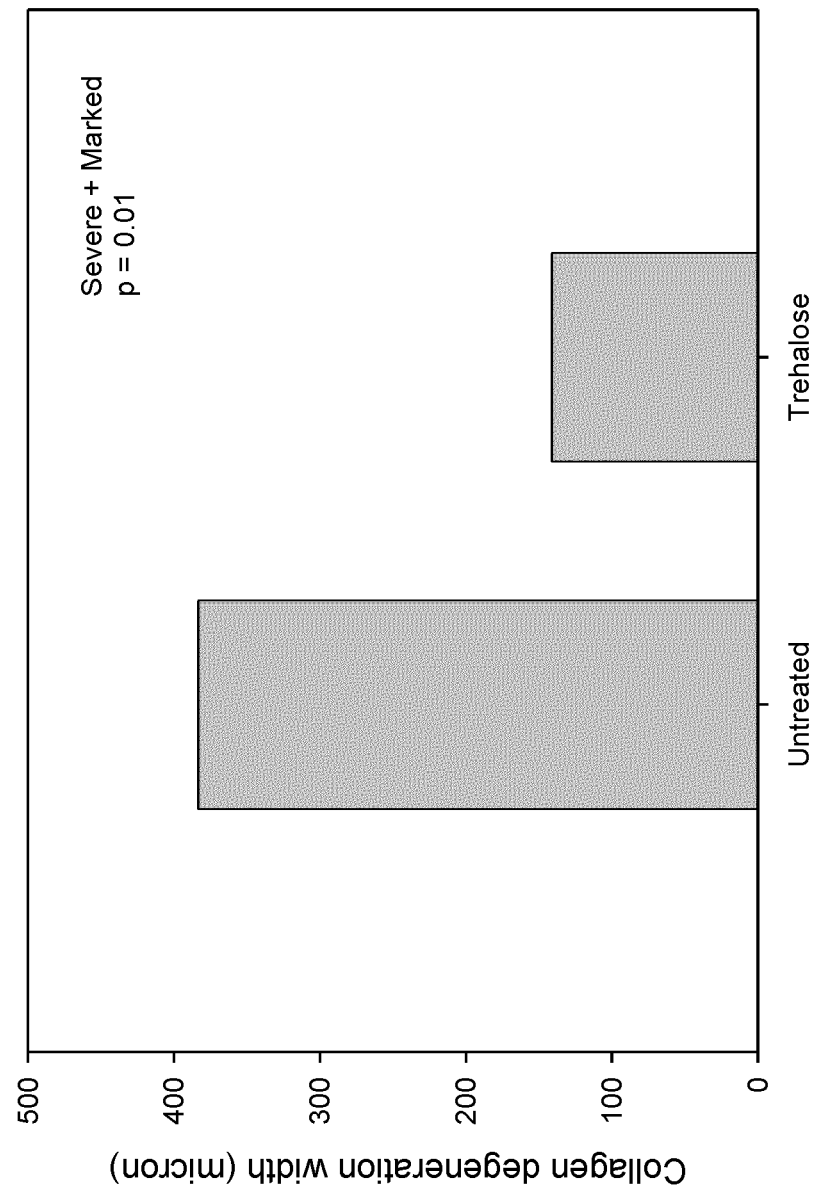
FIG. 7 is a graph comparing collagen degradation in the rat MMT model that received the intra-articular injections of trehalose to those that received no treatment.

Cartilage preservation also correlated to the extent of collagen degeneration. FIG. 7 shows that trehalose significantly reduced the width of cartilage lesions which exhibit collagen depletion characterized as either marked or severe, as measured using an ocular micrometer to assess the cross sectional thickness of cartilage exhibiting reduced collagen staining. The extent of collagen degeneration is defined as follows:

Severe damage (total or near total loss of collagen to tidemark, >90% thickness)

Marked damage (extends through 61-90% of the cartilage thickness)

Moderate damage (extends thru 31-60% of the cartilage thickness)

Mild damage (extends through 11-30% of the cartilage thickness)

Minimal damage (very superficial, affecting upper 10% only)

Figure 8:
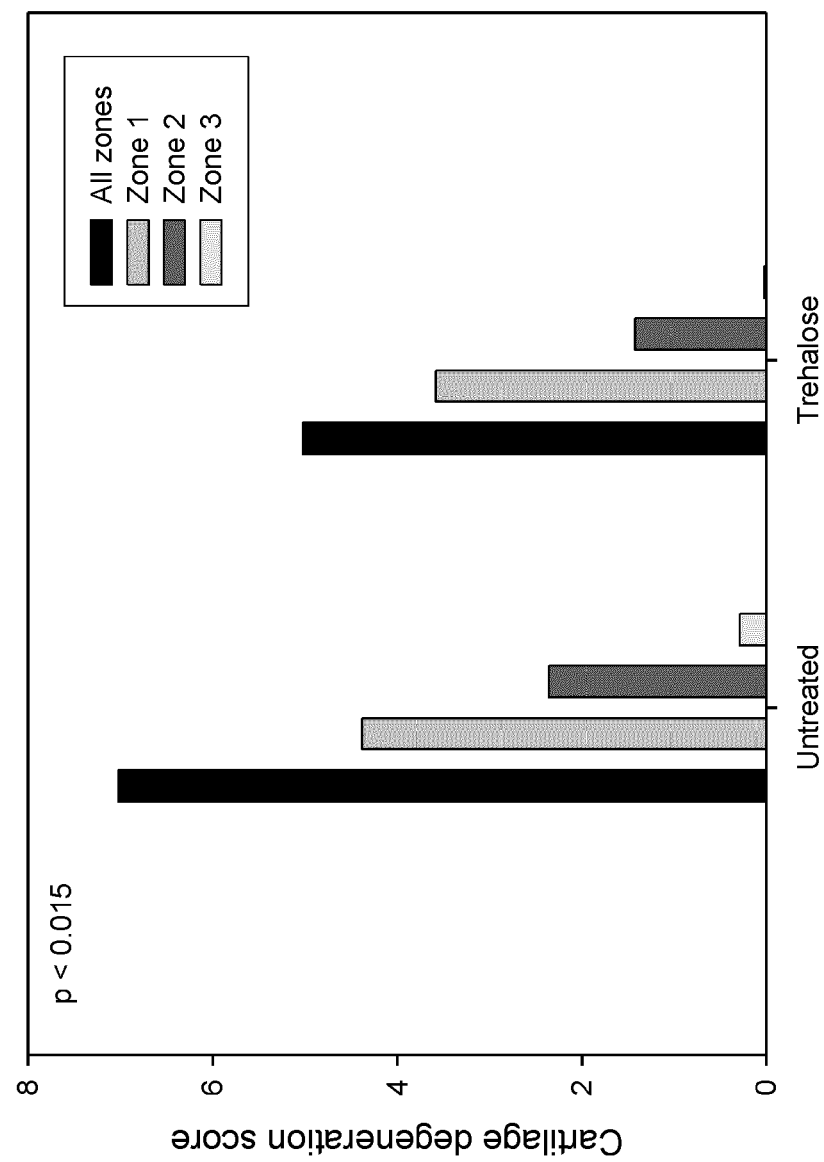
FIG. 8 shows the effect trehalose had on cartilage degeneration of the medial tibial plateau.

Trehalose also improved cartilage degeneration scores, which is a measure of the cellular viability of the remaining cartilage. Cartilage degeneration scores were determined histologically by estimating the area of non-viable (significant chondrocyte and proteoglycan loss but collagen retention) and completely absent cartilage matrix, then estimating the percentage of that area compared to the area of the extrapolated original cartilage cross sectional area. A score of 1-5 is assigned, with a score of 1 indicating cartilage degeneration of 10% or less, and a score of 5 indicating complete cartilage degeneration. In FIG. 8, Zone 1 refers to the one third of the medial tibial plateau closest to the transected meniscus. Zone 1 is the area having the most severe cartilage damage in the MMT model, and was considered extremely challenging as a target for OA therapies. Zone 3 is the one third of the tibial plateau furthest from the surgical site, and sustained the least amount of cartilage damage. Zone 2 was considered to be the area of intermediate cartilage damage and represented a reasonable target for OA therapies. Trehalose statistically improved cartilage degeneration score in all three zones.

Example 4

Rabbit ACLT Model of Osteoarthritis

The trehalose formulation (a 5% trehalose solution in 3 mM glycine-HCl buffer having a pH of approximately 3) described above was also tested in the rabbit anterior cruciate ligament transection (ACLT) model of OA. The ACLT surgery destabilized the rabbit knee to a greater extent than meniscal transection, resulting in not only substantial cartilage deterioration but also osteophyte formation. Studies investigating the development and regulation of osteophyte formation in the rabbit model of OA have detected plate-like formations as early as 4 weeks post-ACLT, and osteophyte growth in all compartments of the knee by 12 weeks post-ACLT.

Rabbits were anesthetized. The patellar fat pad was retracted, and the ACL was isolated. The anterior cruciate ligament was severed with a surgical blade. The fibrous capsule and subcutaneous tissue were closed prior to the skin being sutured. Beginning one week after surgery, intra-articular injections were given weekly for seven weeks, followed by euthanasia at 8 weeks. Cartilage degradation was determined histologically using a modified Mankin scale. Higher scores indicated more extensive cartilage degradation, with a maximum score of 18.

Figure 9:
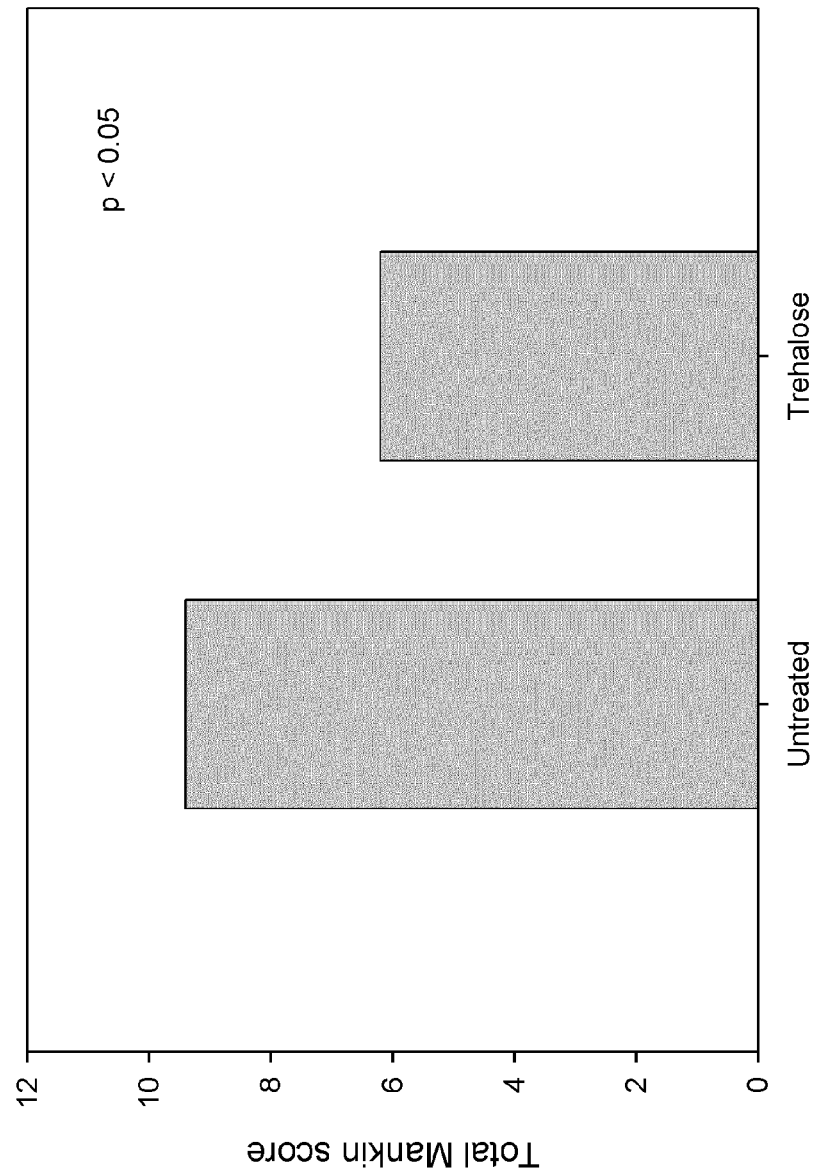
FIG. 9 shows the effect trehalose had on cartilage degradation in a rabbit anterior cruciate ligament transection (ACLT) model of osteoarthritis.

As shown in FIG. 9, the trehalose formulation gave a significant improvement in modified Mankin score compared to untreated animals. (n=15), indicating decreased cartilage degeneration as a result of the intra-articular trehalose injections.

Terminology

A "therapeutically effective amount" or "effective amount" is that amount of an agent to achieve a pharmacological effect. The term "therapeutically effective amount" includes, for example, a prophylactically effective amount. An "effective amount" is an amount effective to achieve a desired pharmacologic effect or therapeutic improvement without undue adverse side effects. For example, an effective amount refers to an amount that increases operativity, quality of life, increases the ability of the patient to increase mobility, or increases weight bearing load, or decreases pain, or increases growth in the bone and cartilage of one or more joints, or reduces joint distortion, pain, swelling, or stiffness. The effective amount of an agent will be selected by those skilled in the art depending on the particular patient and the disease level. It is understood that "an effect amount" or "a therapeutically effective amount" can vary from subject to subject, due to variation in metabolism of therapeutic agents and/or prokinetic agents, age, weight, general condition of the subject, the condition being treated, the severity of the condition being treated, and the judgment of the prescribing physician.

"Treat" or "treatment" refers to any treatment of a disorder or disease associated with bone, cartilage, of soft tissue (such as the synovium) disorder, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder. Thus, as used herein, the term "treat" is used synonymously with the term "prevent."

By "co-administered" is meant simultaneous administration in the same formulation or in two different formulations that are combined into one formulation for administration. In one embodiment, the HA and the other component are co-administered via delivery in the same formulation.

The term "subject" as used herein refers to an animal, in one embodiment, a mammal and in another embodiment, a human, who can benefit from the compositions and methods of the present invention. There is no limitation on the type of animal that could benefit from the present methods. A subject regardless of whether a human or non-human animal may be referred to as an individual, subject, animal, host or recipient. The methods of the present invention have applications in human medicine, veterinary medicine as well as in general, domestic or wild animal husbandry. In one embodiment, the candidate subject is a mammal such as a human, laboratory test animal, such as a mouse, rat, rabbit, guinea pig, hamster or avian species, such as a poultry bird and veterinary medical animal, such as dog, cat, horse, cow, sheep, etc.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A composition for treating a joint condition, comprising:
    a formulation comprising high molecular weight hyaluronic acid (HA); and
    at least one stabilizer, wherein the stabilizer increases stability of the formulation, wherein the at least one stabilizer comprises trehalose, and wherein the trehalose is present in a range of about 0.1% to 50% by weight of the composition.

2. The composition of claim 1, wherein the high molecular weight HA has a molecular weight in the range of about 1 MDa to 6 MDa.

3. The composition of claim 1, wherein the HA is present at a liquid concentration of at least about 1 mg/ml.

4. The composition of claim 1, wherein the HA is lyophilized.

5. The composition of claim 1, wherein the at least one stabilizer further comprises at least one of tocopherol, tocopherol derivatives, mannitol, and sucrose.

6. The composition of claim 1, wherein the formulation is stable at room temperature.

7. The composition of claim 1, further comprising at least one additional component.

8. The composition of claim 7, wherein the additional component is selected from the group consisting of a glycosaminoglycan (GAG) and a GAG precursor and is present within the composition at a ratio of HA to additional component in the range of about 1:0.005 to 1:100.

9. A kit, comprising:
    a composition of high molecular weight hyaluronic acid (HA) and at least one stabilizer, wherein the at least one stabilizer comprises trehalose, and wherein the trehalose is present in a rang of about 0.1% to 50% by weight of the composition; and
    a syringe comprising the composition of HA and stabilizer in a single chamber.

10. The kit of claim 9, wherein the HA has a molecular weight greater than 1 MDa.

11. The kit of claim 9, wherein the HA is present at a liquid concentration of at least about 1 mg/ml.

12. The kit of claim 9, wherein the HA is lyophilized.

13. The kit of claim 9, wherein the at least one stabilizer further comprises at least one of tocopherol, tocopherol derivatives, mannitol, and sucrose.

14. The kit of claim 9, wherein the composition further comprises at least one additional component selected from the group consisting of a glycosaminoglycan (GAG) and a GAG precursor.

15. The kit of claim 14, wherein the syringe further comprises a separate chamber that comprises the at least one additional component.

16. The kit of claim 14, wherein the at least one additional component is lyophilized.

17. A method for treating joints, comprising:
    administering a formulation comprising high molecular weight hyaluronic acid and at least one stabilizer to a subject in need thereof, wherein the at least one stabilizer comprises trehalose, and wherein the trehalose is present in a range of about 0.1% to 50% by weight of the composition.

18. The method of claim 17, wherein the step of administering further comprises storing the formulation at room temperature prior to administration.

19. The method of claim 17, wherein the step of administering further comprises combining the formulation with at least one additional component prior to administration.

* * * * *